US010769823B2

(12) United States Patent
Igarashi et al.

(10) Patent No.: US 10,769,823 B2
(45) Date of Patent: Sep. 8, 2020

(54) IMAGE PROCESSING APPARATUS, MAGNETIC RESONANCE IMAGING APPARATUS, AND STORAGE MEDIUM

(71) Applicant: Canon Medical Systems Corporation, Otawara-shi (JP)

(72) Inventors: Takuma Igarashi, Nasushiobara (JP); Ryo Shiroishi, Nasushiobara (JP)

(73) Assignee: Canon Medical Systems Corporation, Otawara-shi (JP)

(*) Notice: Subject to any disclaimer, the term of this patent is extended or adjusted under 35 U.S.C. 154(b) by 154 days.

(21) Appl. No.: 15/996,556

(22) Filed: Jun. 4, 2018

(65) Prior Publication Data

US 2018/0374246 A1     Dec. 27, 2018

(30) Foreign Application Priority Data

Jun. 22, 2017  (JP) ................................ 2017-122454
May 14, 2018  (JP) ................................ 2018-093280

(51) Int. Cl.
  *G06K 9/00*  (2006.01)
  *G06T 11/00*  (2006.01)
  (Continued)

(52) U.S. Cl.
  CPC .......... *G06T 11/008* (2013.01); *A61B 5/0042* (2013.01); *A61B 5/055* (2013.01);
  (Continued)

(58) Field of Classification Search
  CPC ..... A61B 5/0042; A61B 5/055; A61B 5/4088; A61B 5/7267; G01R 33/5602;
  (Continued)

(56) References Cited

U.S. PATENT DOCUMENTS

2010/0127704 A1* 5/2010 Warntjes ................ G01R 33/56
                                                                 324/309
2015/0018664 A1* 1/2015 Pereira ................... A61B 5/055
                                                                 600/410
(Continued)

FOREIGN PATENT DOCUMENTS

JP          2013-192057          9/2013
JP          2016-225862         12/2016

OTHER PUBLICATIONS

Warntjes, J.B.M., et al., "Rapid Magnetic Resonance Quantification on the Brain: Optimization for Clinical Usage", Magnetic Resonance in Medicine 60:320-329 (2008), 10 pages.

*Primary Examiner* — Xin Jia
(74) *Attorney, Agent, or Firm* — Oblon, McClelland, Maier & Neustadt, L.L.P.

(57) ABSTRACT

An image processing apparatus according to an embodiment includes a processing circuitry. The processing circuitry obtains an MR image acquired by a magnetic resonance imaging apparatus and related to a brain. The processing circuitry divides a region of the brain in the MR image, into plural regions. The processing circuitry sets a parameter value used in generation of a calculated image generated by synthetic MRI and related to the brain, such that a relation of contrast among regions included in the plural regions becomes a predetermined relation. The processing circuitry generates the calculated image by the synthetic MRI, by using the MR image and the parameter value.

17 Claims, 11 Drawing Sheets

(51) Int. Cl.
   *G01R 33/56*   (2006.01)
   *A61B 5/00*    (2006.01)
   *G06T 5/00*    (2006.01)
   *A61B 5/055*   (2006.01)

(52) U.S. Cl.
   CPC ..... *G01R 33/5602* (2013.01); *G01R 33/5608*
            (2013.01); *G06T 5/008* (2013.01); *A61B*
            *5/4088* (2013.01); *A61B 5/7267* (2013.01);
                    *G06T 2207/10088* (2013.01); *G06T*
                    *2207/20081* (2013.01); *G06T 2207/20084*
                    (2013.01); *G06T 2207/30016* (2013.01)

(58) Field of Classification Search
   CPC .............. G01R 33/5608; G06T 11/008; G06T
                    2207/10088; G06T 2207/20081; G06T
                    2207/20084; G06T 2207/30016; G06T
                                                5/008
   See application file for complete search history.

(56) References Cited

U.S. PATENT DOCUMENTS

2017/0154419 A1*  6/2017  Shiroishi ................ G06T 5/009
2018/0017652 A1*  1/2018  Ye ....................... G01R 33/5608
2018/0077298 A1   3/2018  Matsunaga
2018/0303373 A1* 10/2018  Freeman ............ G01R 33/5601

* cited by examiner

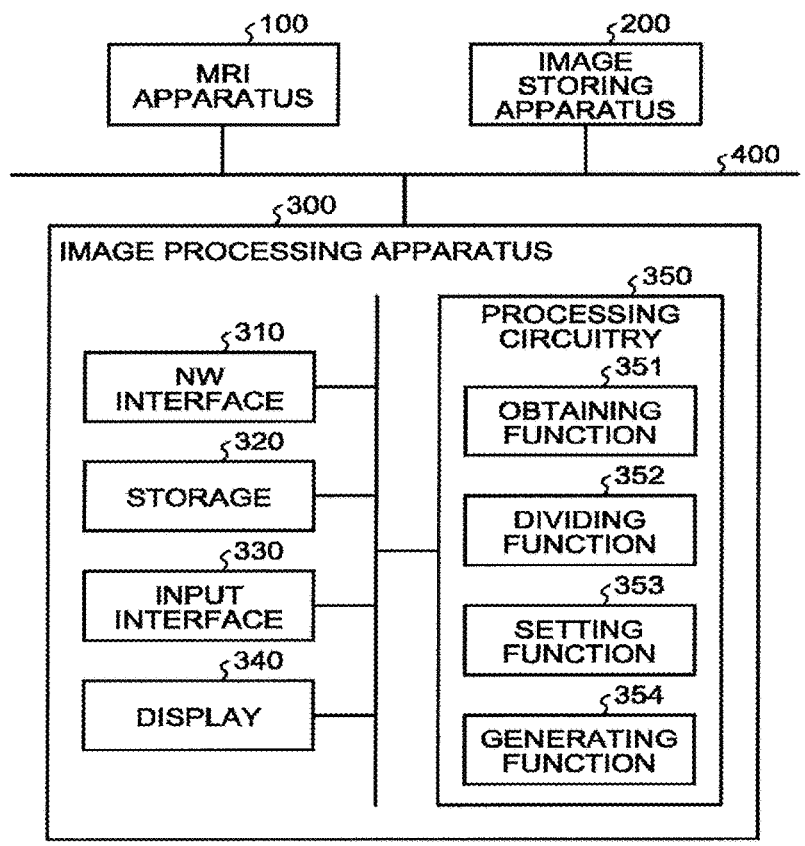

FIG.3

| IMAGE TYPE | GM | WM | CSF |
|---|---|---|---|
| T1W | 1 | 1.05 | 0.1 |
| T2W | 2.52 | 1 | 3 |
| FLAIR | 2.1 | 1 | 0.1 |

FIG.4

| IMAGE TYPE | IMAGING METHOD | TR | TE | TI |
|---|---|---|---|---|
| T1W | SE | 100 TO 1000 | 1 TO 50 | |
| T2W | SE | 3000 TO 10000 | 80 TO 120 | |
| FLAIR | IR | 3000 TO 10000 | 80 TO 120 | 2300 TO 3500 |

FIG.5A
| IMAGE TYPE | GM | WM | CSF |
|---|---|---|---|
| FLAIR | 2.1 | 1 | 0 |
FIG.5B
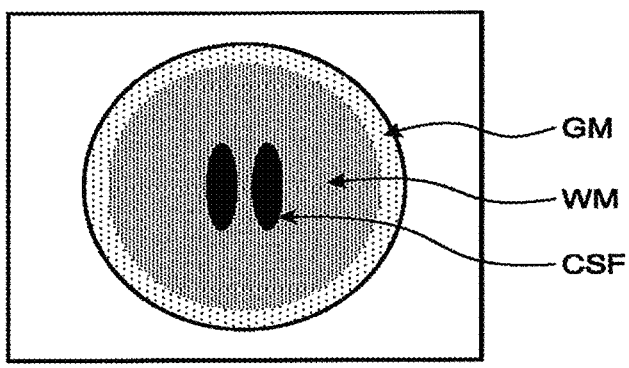
FIG.5C
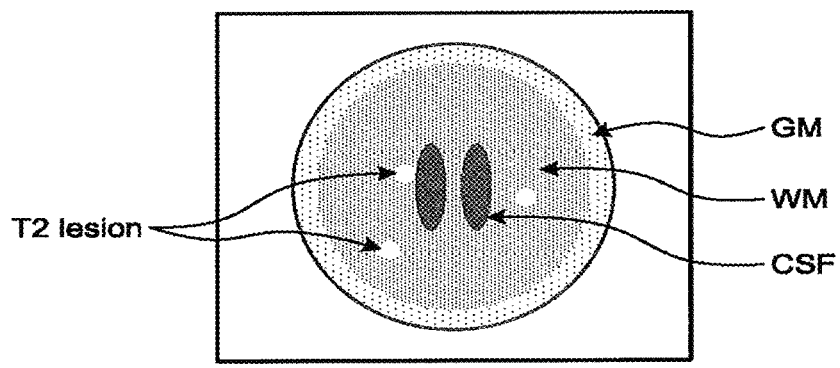
FIG.5D
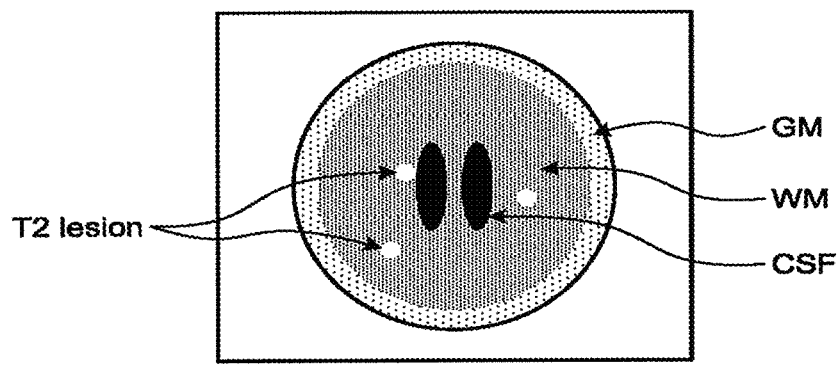

FIG. 6A
| IMAGE TYPE | GM | WM | CSF |
|---|---|---|---|
| FLAIR | 2.1 | 1 | 0 |
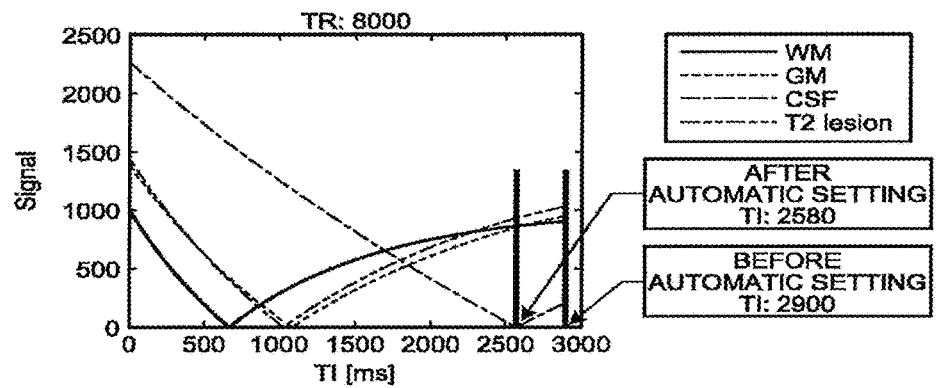
FIG. 6B
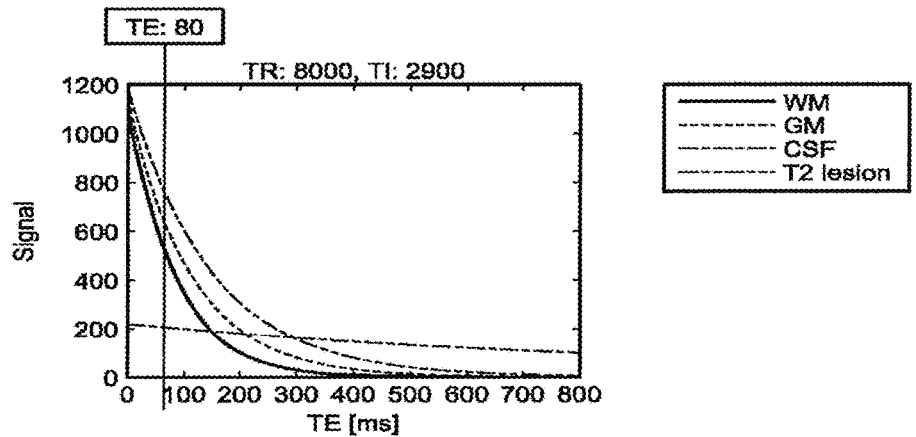
FIG. 6C
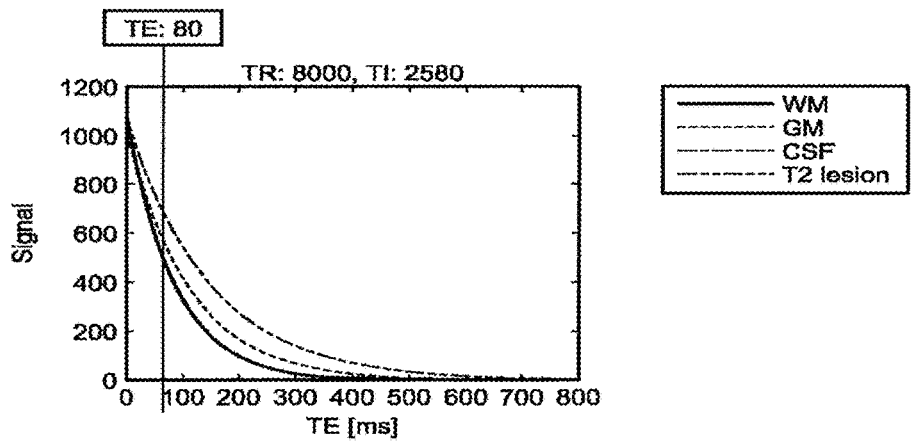
FIG. 6D

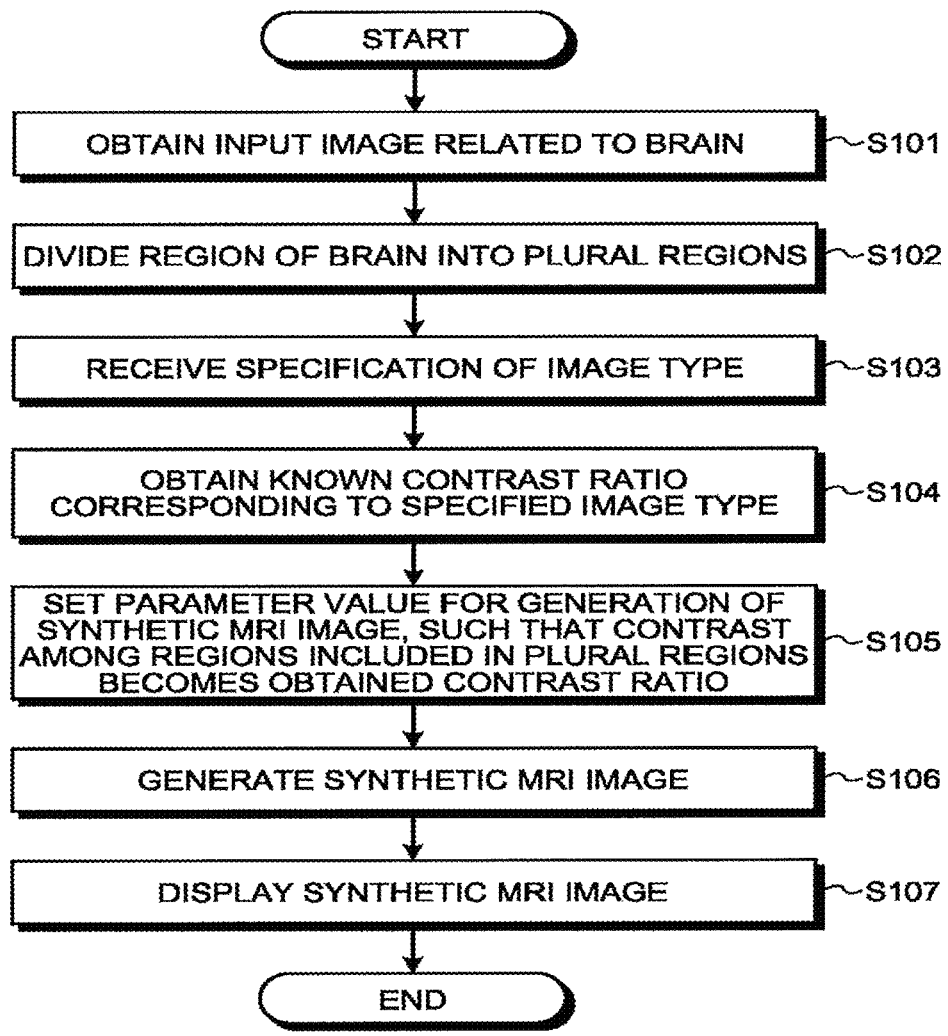

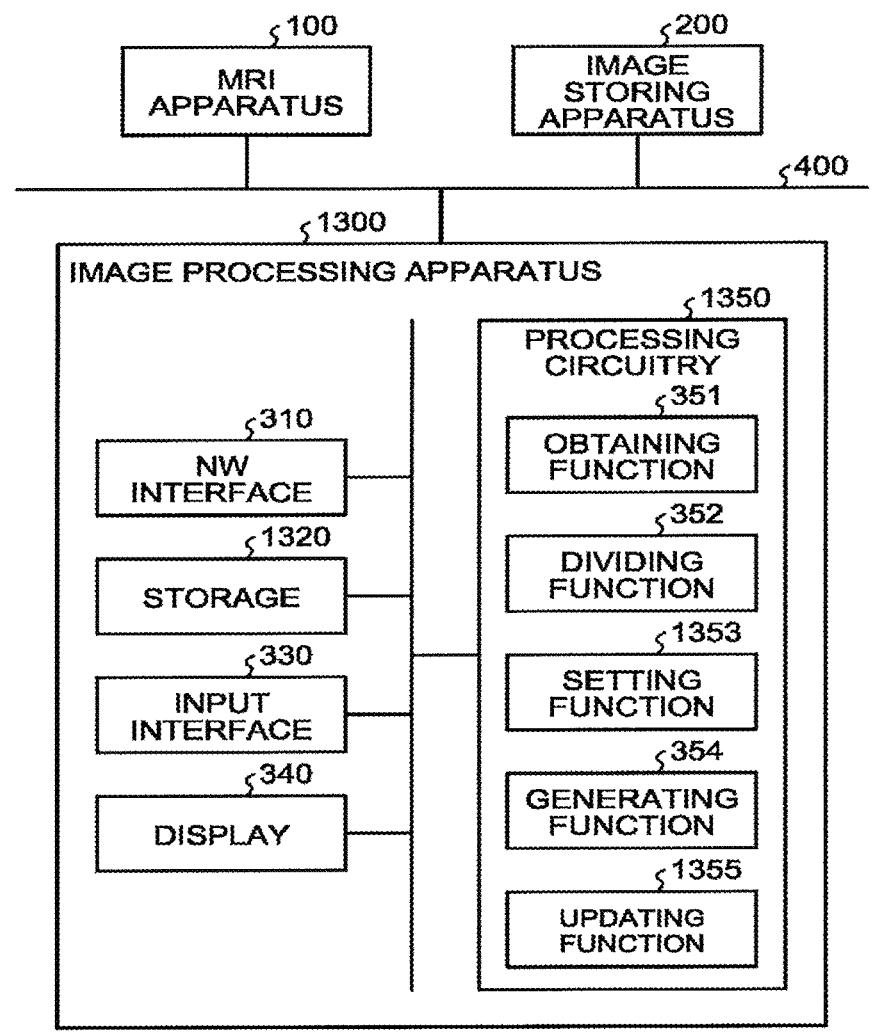

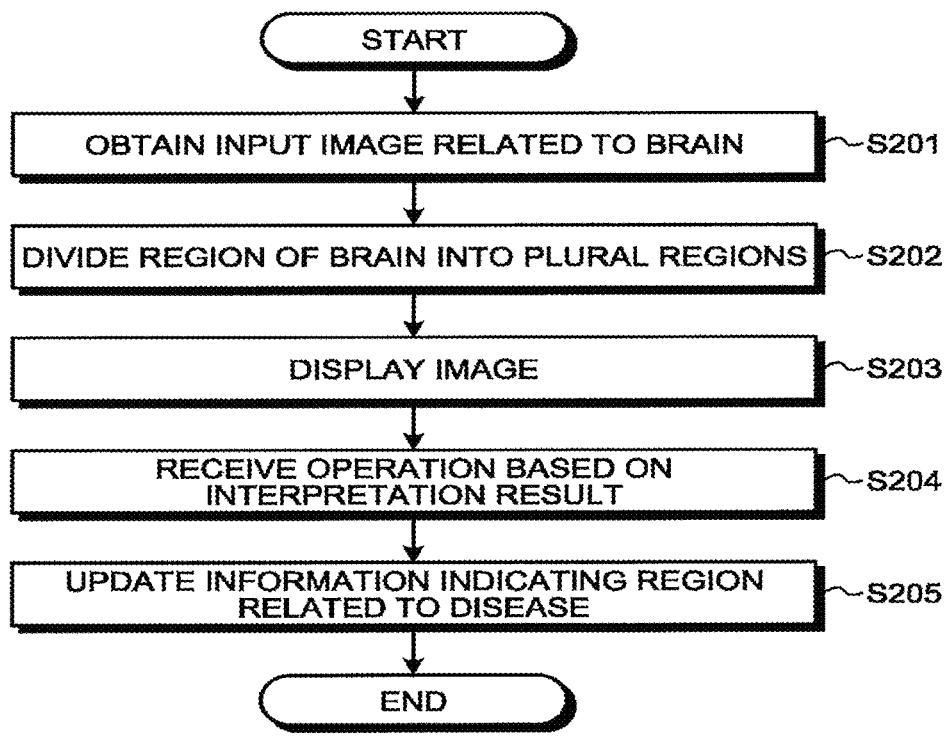

IMAGE PROCESSING APPARATUS, MAGNETIC RESONANCE IMAGING APPARATUS, AND STORAGE MEDIUM

CROSS-REFERENCE TO RELATED APPLICATIONS

This application is based upon and claims the benefit of priority from Japanese Patent Application No. 2017-122454, filed on Jun. 22, 2017 and Japanese Patent Application No. 2018-093280, filed on May 14, 2018; the entire contents of all of which are incorporated herein by reference.

FIELD

Embodiments described herein relate generally to an image processing apparatus, a magnetic resonance imaging apparatus, and a storage medium.

BACKGROUND

Conventionally, a technique, which is for calculative generation of calculated images of arbitrary image types after imaging, by use of magnetic resonance (MR) images acquired by magnetic resonance imaging (MRI) apparatuses and arbitrary parameter values, has been known. This technique for generation of calculated images has advantages over a case where images are generated while data are actually collected, in that examination is able to be performed in a shorter time period and the parameter values are able to be set after data collection.

BRIEF DESCRIPTION OF THE DRAWINGS

FIG. 1 is a diagram illustrating an example of a configuration of an image processing apparatus according to a first embodiment;

FIG. 2 is a diagram illustrating an example of plural regions of a brain, according to the first embodiment;

FIG. 3 is a diagram illustrating an example of a contrast ratio table stored in a storage according to the first embodiment;

FIG. 4 is a diagram illustrating an example of a parameter range table stored in the storage according to the first embodiment;

FIGS. 5A to 5D are diagrams illustrating a specific example of a calculated image generated by the image processing apparatus according to the first embodiment;

FIGS. 6A to 6D are diagrams illustrating a specific example of a calculated image generated by the image processing apparatus according to the first embodiment;

FIG. 7 is a flow chart illustrating a procedure of processing executed by the image processing apparatus according to the first embodiment, the processing being related to generation of a calculated image;

FIG. 9 is a diagram illustrating an example of a configuration of an image processing apparatus according to a second embodiment;

FIG. 10 is a diagram illustrating an example of a disease-related region table stored in a storage according to the second embodiment;

FIG. 11 is a flow chart illustrating a procedure of processing related to updating of a disease-related region table executed by the image processing apparatus according to the second embodiment;

DETAILED DESCRIPTION

Figure 8A:
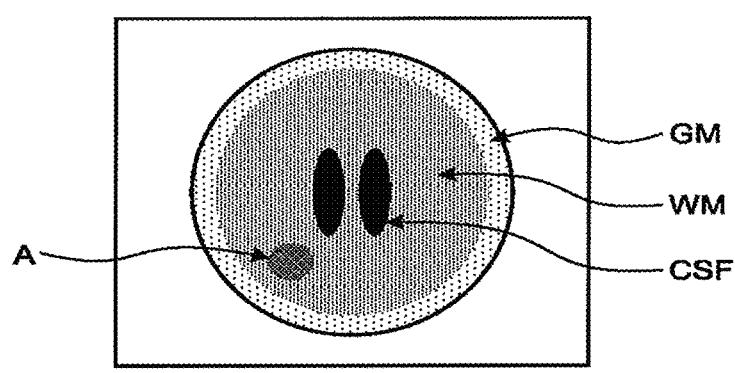
FIGS. 8A and 8B are diagrams illustrating an example of effects according to the first embodiment.

An image processing apparatus according to an embodiment includes an obtaining unit, a dividing unit, a setting unit, and a generating unit. The obtaining unit obtains an MR image acquired by a magnetic resonance imaging apparatus and related to a brain. The dividing unit divides a region of the brain in the MR image obtained by the obtaining unit, into plural regions. The setting unit sets a parameter value used in generation of a calculated image generated by synthetic MRI and related to the brain, such that a relation of contrast among regions included in the plural regions becomes a predetermined relation in the calculated image. The generating unit generates the calculated image by the synthetic MRI by using: the MR image obtained by the obtaining unit; and the parameter value set by the setting unit.

Hereinafter, while reference is made to the drawings, image processing apparatuses, magnetic resonance imaging apparatuses, and storage media, according to embodiments, will be described in detail.

First Embodiment

FIG. 1 is a diagram illustrating an example of a configuration of an image processing apparatus according to a first embodiment. For example, as illustrated in FIG. 1, in this embodiment, an MRI apparatus 100, an image storing apparatus 200, and an image processing apparatus 300 are communicatably connected via a network 400.

The MRI apparatus 100 collects image data of a subject by using the magnetic resonance imaging phenomenon. Specifically, the MRI apparatus 100 collects magnetic resonance data from the subject, by executing various imaging sequences based on imaging conditions set by an operator. The MRI apparatus 100 generates two-dimensional or three-dimensional image data (an MR image) by executing image processing, such as Fourier transform processing, on the collected magnetic resonance data.

The image storing apparatus 20 stores the image data collected by the MRI apparatus 100. Specifically, the image storing apparatus 200 obtains the image data from the MRI apparatus 100 via the network 400, and causes a storage to store therein the obtained image data, the storage being provided in or outside the image storing apparatus 200. For example, the image storing apparatus 200 is realized by a computer device, such as a server apparatus.

The image processing apparatus 300 processes the image data collected by the MRI apparatus 100. Specifically, the image processing apparatus 300 obtains the image data from the MRI apparatus 100 or the image storing apparatus 200, via the network 400, and causes a storage to store therein the obtained image data, the storage being provided in or outside the image processing apparatus 300. Further, the image processing apparatus 300 executes various types of image processing on the obtained image data, and displays the yet to be image-processed image data or the image-processed image data, on a display or the like. For example, the image processing apparatus 300 is realized by a computer device, such as a work station.

Specifically, the image processing apparatus 300 includes a network (NW) interface 310, a storage 320, an input interface 330, a display 340, and a processing circuitry 350.

The NW interface 310 controls transmission and communication of various data transmitted and received between the image processing apparatus 300 and the other apparatuses connected via the network 400. Specifically, the NW interface 310 is connected to the processing circuitry 350, converts image data output from the processing circuitry 350, into a format conforming to a predetermined communication protocol, and transmits the converted image data to the MRI apparatus 100 or the image storing apparatus 200. Further, the NW interface 310 outputs image data received from the MRI apparatus 100 or the image storing apparatus 200, to the processing circuitry 350. For example, the NW interface 310 is realized by a network card, a network adapter, or a network interface controller (NIC).

The storage 320 stores therein various data. Specifically, the storage 320 is connected to the processing circuitry 350, and stores therein image data input thereto, or outputs image data stored therein to the processing circuitry 350, according to a command transmitted from the processing circuitry 350. For example, the storage 320 is realized by: a semiconductor memory element, such as a random access memory (RAM) or a flash memory; a hard disk; or an optical disk.

The input interface 330 receives input operations for various instructions and various types of information, from an operator. Specifically, the input interface 330 is connected to the processing circuitry 350, converts an input operation received from the operator to an electric signal, and outputs the electric signal to a control circuit. For example, the input interface 330 is realized by any of: a trackball for setting a region of interest (ROI); a switch button; a mouse; a keyboard; a touch pad for performing an input operation through contact with an operation surface; a touch screen having a display screen and a touch pad that are integrated together; a non-contact input interface using an optical sensor; and a voice input interface. In this specification, the input interface 330 is not limited only to an input interface having physical operating components, such as a mouse and a keyboard. For example, an electric signal processing circuitry that receives an electric signal corresponding to an input operation from an external input device provided separately from the image processing apparatus 300 and outputs this electric signal to a control circuit is also included in examples of the input interface 330.

The display 340 displays thereon various types of information and various images. Specifically, the display 340 is connected to the processing circuitry 350, and displays thereon images in various formats, based on image data output from the processing circuitry 350. For example, the display 340 is realized by a liquid crystal monitor, a cathode ray tube (CRT) monitor, or a touch panel.

According to input operations received from an operator via the input interface 330, the processing circuitry 350 controls the components included in the image processing apparatus 300. Specifically, the processing circuitry 350 causes the storage 320 to store therein image data output from the NW interface 310. Further, the processing circuitry 350 displays image data read from the storage 320, on the display 340. For example, the processing circuitry 350 is realized by a processor.

Based on such a configuration, the image processing apparatus 300 according to this embodiment has a function of calculatively generating a calculated image of an arbitrary image type after imaging, by using an MR image acquired by the MRI apparatus 100 and an arbitrary parameter value. Image types include, for example, T1 weighted (T1W) image, T2 weighted (T2W) image, and fluid attenuation inversion recovery (FLAIR) image.

For example, the image processing apparatus 300 has a function of generating a calculated image (synthetic MRI image) by synthetic MRI. Specifically, the image processing apparatus 300 derives tissue quantitative values, such as a T1 value, a T2 value, and a proton density (PD) value, by using MR images acquired while inversion time (TI), echo time (TE), and flip angle (FA) are changed, through simulation or curve fitting using a theoretical formula for signal values of MR images. The image processing apparatus 300 then generates, based on the derived tissue quantitative values, a calculated image of an arbitrary image type, according to arbitrary parameter values of TI, TE, and repetition time (TR). For example, the image processing apparatus 300 obtains a T1 relaxation curve from plural TI images, and derives a T1 value and a PD value from the curve. Further, for example, the image processing apparatus 300 derives a T2 value from plural TE images, and generates a calculated image of an arbitrary image type, based on these quantitative values.

In synthetic MRI, by quantification of a T1 value, a T2 value, and a proton density, a calculated image of an arbitrary type is able to generated. Further, in synthetic MRI, even if a calculated image of a different image type is to be obtained, there is no need for imaging to be performed again. Furthermore, in synthetic MRI, even after a calculated image has been generated once, parameter values of TR, TE, and TI are able to be adjusted freely, and even in the process of this adjustment, a calculated images having contrast under that condition is able to be generated in real time.

The image processing apparatus 300 according to this embodiment is configured to be able to obtain a calculated image suitable for diagnosis.

Generally, use of such calculated images aims to shorten the time needed for examination using MR images, by calculative obtainment of images having the same contrast as MR images that have been conventionally obtained by imaging. For this aim, a calculated image is often generated with parameter values that are the same as those for imaging, but even if the parameter values are the same as those for imaging, contrast of the generated calculated image may not become the same as that of an MR image obtained by imaging. In this case, for obtainment of a calculated image having intended contrast, parameter values need to be adjusted while contrast of the calculated image is checked every time, and the examination time may not be shortened because of this adjustment.

Therefore, the image processing apparatus 300 according to this embodiment is configured to enable the examination time to be shortened by automatically setting parameter values allowing a calculated image to be obtained, the calculated image having the same contrast as an MR image that has conventionally been obtained by imaging.

Specifically, in this embodiment, the storage 320 stores therein, for each image type, with respect to contrast among regions included in plural regions of a brain, information indicating a known contrast ratio corresponding to the image type. The storage 320 according to this embodiment is an example of the storage.

Plural regions (also called parcels) of a brain are, for example, regions resulting from division of a region of a brain according to anatomical structures and functions.

FIG. 2 is a diagram illustrating an example of plural regions of a brain, according to the first embodiment. For example, as illustrated in FIG. 2, a region of the brain is defined by being divided stage by stage in plural levels, and is defined such that the lower the level is, the finer the units of the division is. For example, in the example illustrated in FIG. 2, each level is expressed as Level-n (n=0, 1, 2, 3, 4, 5, ...), and the larger the n is, the lower the level is. In FIG. 2, only Level-3 to Level-5 are illustrated.

For example, Level-0 represents the region of the whole brain. Further, for example, the "limbic system" at Level-3 and the "limbic system" at Level-4 have the same region name, but different sizes. For example, the "limbic system" at Level-3 is a unit that is generally called a "limbic system." At Level-4, the "limbic system" of Level-3 is divided into a "cingulate gyrus", an "amygdala", a "hippocampus", and other regions, and the "other regions" referred to herein are defined as the "limbic system".

Further, in the example illustrated in FIG. 2: the "limbic system" of Level-4 is divided into a "parahippocampalis gyrus" and a "gyrusentcrhinal area" at Level-5; the "cingulate gyrus" of Level-4 is divided into a "posterior cingulate gyros", etc. (not illustrated) at Level-5; and the "amygdala" and the "hippocampus" of Level-4 are each divided into one or plural regions (not illustrated) at Level-5.

When a region of a brain is divided in units different among levels, individual region units at each levels may each be one region of plural regions of the brain referred to in this application. For example, each of the "limbic system" of Level-3, the "limbic system" of Level-4, the "hippocampus" of Level-4, and the "parahippocampalis gyrus" of Level-5 may be one region.

For example, plural regions of a brain referred to in this application are defined in units of regions at any one level (for example, the lowest level). Or, plural regions of a brain referred to in this application may be defined in a combination of units of regions in different levels, for example, as a combination of the "parahippocampalis gyros" and "gyrusentcrhinal area" of Level-5, and the "cingulate gyrus", "amygdala", and "hippocampus" of Level-4.

Based on such plural regions of a brain, the storage 320 stores therein, for each image type, with respect to contrast among regions included in the plural regions of the brain, information indicating a known contrast ratio corresponding to the image type.

FIG. 3 is a diagram illustrating an example of a contrast ratio table stored in the storage 320 according to the first embodiment. For example, as illustrated in FIG. 3, the storage 320 stores therein, a contrast ratio table associating, for each image type, the image type with a known contrast ratio corresponding to plural regions of a brain.

For example, "T1W", "T2W", and "FLAIR" illustrated in FIG. 3 each represent an image type, "T1W" representing T1W image, "T2W" representing T2W image, "FLAIR" representing FLAIR image. Further, "GM", "WM", and "CSF" illustrated in FIG. 3 each represent a region of a brain, "GM" representing a region of grey matter, "WM" representing a region of white matter, "CSF" representing a region of cerebrospinal fluid.

For example, the example illustrated in FIG. 3 indicates that a known contrast ratio corresponding to a T1W image is grey matter:white matter:cerebrospinal fluid=1:1.05:0.1. Further, the example illustrated in FIG. 3 indicates that a known contrast ratio corresponding to a T2W image is grey matter:white matter:cerebrospinal fluid=2.52:1:3. Furthermore, the example illustrated in FIG. 3 indicates that a known contrast ratio corresponding to a FLAIR image is grey matter:white matter:cerebrospinal fluid=2.1:1:0.1.

Further, in this embodiment, the storage 320 stores therein, for each image type, information defining ranges of parameter values, the ranges serving as conditions for setting of parameter values used in generation of a calculated image.

FIG. 4 is a diagram illustrating an example of a parameter range table stored in the storage 320 according to the first embodiment. For example, as illustrated in FIG. 4, the storage 320 stores therein a parameter range table associating, for each image type, the image type, an imaging method, a range of parameter values of each of plural parameters used in generation of a calculated image, with one another.

For example, "T1W", "T2W", and "FLAIR" illustrated in FIG. 4 each represent an image type, "T1W" representing T1W image, "T2W" representing T2W image, "FLAIR" representing FLAIR image. Further, "SE" and "IR" illustrated in FIG. 4 each represent an imaging method, "SE" representing the spin echo (SE) method, "IR" representing the inversion recovery (IR) method. Furthermore, "TR", "TE", and "TI" illustrated in FIG. 4 respectively represent plural parameters used in generation of a calculated image, "TR" representing TR, "TE" representing TE, "TI" representing TI.

For example, the example illustrated in FIG. 4 indicates that a range of TR is 100 to 1000 and a range of TE is 1 to 50, the ranges corresponding to a T1W image and the SE method. Further, for example, the example illustrated in FIG. 4 indicates that a range of TR is 3000 to 10000 and a range of TE is 80 to 120, the ranges corresponding to a T2W image and the SE method. Furthermore, for example, the example illustrated in FIG. 4 indicates that a range of TR is 3000 to 10000 and a range of TE is 80 to 120, the ranges corresponding to a FLAIR image and the IR method.

Herein, for example, as each range of parameter values set in the parameter range table, for each image type, a range of general parameter values, which is used when MR images of the same image type are acquired by conventional imaging, is set. Thereby, parameter values for generation of a calculated image are able to be set in ranges of parameter values generally used in the medical field, and calculated images following the common practice in the medical field are thus able to be generated.

Further, in this embodiment, the processing circuitry 350 has an obtaining function 351, a dividing function 352, a setting function 353, and a generating function 354. The dividing function 352 according to this embodiment is an example of the dividing unit. Further, the setting function 353 according to this embodiment is an example of the setting unit. Furthermore, the generating function 354 according to this embodiment is an example of the generating unit. The dividing unit, the setting unit, and the generating unit according to this specification may be realized by mixture of hardware, such as a circuit, and software.

The obtaining function 351 obtains input images related to the brain of a subject from the MRI apparatus 100 or the image storing apparatus 200.

Specifically, the obtaining function 351 obtains, as the input images: plural MR images acquired by the MRI apparatus 100 while parameter values influencing contrast of the images, such as TI, TE, and FA, are changed; and plural quantitative images, such as a T1 map image, a T2 map image, and a PD image, which have been derived by use of the MR images. For example, the obtaining function 351 obtains T1W images acquired by use of a Magnetization Prepared 2 Rapid Gradient Echo (MP2RAGE) sequence by the MRI apparatus 100, and a T1 map image derived from the T10 images. Or, for example, the obtaining function 351 may obtain, as an input image, one MR image obtained by a sequence enabling, while changing TI, TE, and FA, these changes to be saved in one image.

The dividing function 352 divides a region of a brain in an input image related to the brain, into plural regions.

Specifically, the dividing function 352 uses as an input image that is an MR image obtained by the obtaining function 351, and divides a region of a brain in the input image into plural regions. For example, the dividing function 352 uses, as an input image, a T1W image acquired by use of an MP2RAGE sequence by the MRI apparatus 100, and divides a region of a brain in the input image into plural regions.

Herein, for example, the dividing function 352 executes division (also called parcellation) into plural regions, as exemplified by FIG. 2, by dividing the region of the brain in the input image based on anatomical structures and functions.

The setting function 353 sets parameter values used in generation of a calculated image related to the brain, such that a relation of contrast among regions included in the plural regions of the brain divided by the dividing function 352 in the generated calculated image related to the brain becomes a predetermined relation.

Specifically, the setting function 353 sets parameter values used in generation of a calculated image, such that a relation of contrast among regions included in plural regions in a calculated image related to a brain generated by synthetic MRI becomes a predetermined relation.

In this embodiment, the setting function 353 sets parameter values used in generation of a calculated image, such that contrast among regions included in the plural regions of the brain divided by the dividing function 352 becomes a known contrast ratio corresponding to an image type specified by an operator.

Specifically, the setting function 353 receives specification of the image type from the operator via the input interface 330. For example, the setting function 353 receives the specification of the image type by displaying buttons respectively representing plural image types that have been determined beforehand, on the display 340, and receiving an operation for selection of any one of these buttons, from the operator.

Thereafter, the setting function 353 obtains a known contrast ratio corresponding to the specified image type by referring to the contrast ratio table stored in the storage 320. The setting function 353 then sets parameter values used in generation of a calculated image, such that contrast among regions included in the plural regions divided by the dividing function 352 becomes the known contrast ratio obtained.

The setting function 353 then obtains ranges of parameter values corresponding to the specified image type by referring to the parameter range table stored in the storage 320. The setting function 353 then sets parameter values used in generation of a calculated image, such that a contrast ratio among regions included in the plural regions becomes the closest to the contrast ratio obtained from the contrast ratio table, within the obtained ranges of parameter values.

For example, when parameter values of TE, TR, and TI used in generation of a calculated image are respectively TE, TR, and TI, a combination of these parameter values is expressed as a set θ as follows.

$$\theta = (TR, TE, TI)$$

Further, ranges of parameter values of TE, TR, and TI respectively set in the parameter range table are expressed as follows.

$$TR_{min} < YR < TR_{max}, TE_{min} < TE < TE_{max},$$
$$TI_{min} < TI < TR_{max}$$

For example, when the number of regions of a brain set in the contrast ratio table is N, a contrast ratio among regions in a calculated image derived from parameter values of the set θ is represented by a vector $C_\theta$ composed of a contrast ratio among the regions, as follows.

$$C_\theta = (c1_\theta, c2_\theta, c3_\theta, \ldots, cN_\theta)$$

Further, a contrast ratio among regions set in the contrast ratio table is represented by a vector $C_{DB}$ composed of a contrast ratio among these regions, as follows.

$$C_{DB} = (c1_{DB}, c2_{DB}, c3_{DB}, \ldots, cN_{DB})$$

In this case, the setting function 353 searches for a combination $\theta_{optimized}$ optimized of TE, TR, and TI, at which a distance $D(C_\theta - C_{DB})$ between the vector $C_\theta$ and the vector $C_{DB}$ is minimized, by using a function $D(\cdot)$ representing distance between vectors, as expressed below.

$$\theta_{optimized} = \mathrm{argmin}_\theta D(C_\theta - C_{DB})$$

Specifically, the setting function 353 sequentially derives values of the vector $C_\theta$ and the vector $C_{DB}$, while sequentially changing each of TE, TR, and TI individually within ranges of parameter values obtained from the parameter range table, and further derives values of the distance $D(C_\theta - C_{DB})$ between the vector $C_\theta$ and the vector $C_{DB}$. The setting function 353 then determines $\theta_{optimized}$, which is a combination of TE, TR, and TI, at which the distance $D(C_\theta - C_{DB})$ is minimized.

For example, when changing each parameter value, the setting function 353 does not necessarily change the parameter value to all of values in the range of parameter values obtained from the parameter range table. For example, the setting function 353 calculates the values of the distance $D(C_\theta - C_{DB})$ between the vector $C_\theta$ and the vector $C_{DB}$ while sequentially changing the parameter values such that the parameter values gradually depart from their initial values that are parameter values normally used when the MR images are acquired. The setting function 353 then ends processing at a time point when the distance $D(C_{\theta-CDB})$ has a value smaller than a predetermined threshold, and determines $\theta_{optimized}$, which is a combination of TE, TR, and TI, at that time point.

Thereafter, the setting function 353 respectively sets parameter values of TE, TR, and TI in the determined $\theta_{optimized}$, as parameter values used in generation of a calculated image. Thereby, parameter values used in generation of a calculated image are automatically set, such that contrast among regions included in plural regions of a brain satisfies a known contrast ratio corresponding to a specified image type.

The generating function 354 generates the calculated image by using the input images obtained by the obtaining function 351 and the parameter values set by the setting function 353.

Specifically, the generating function 354 generates calculated image by synthetic MRI, by using a quantitative image obtained by the obtaining function 351 and parameter values set by the setting function 353. For example, the generating function 354 generates a calculated image by using: a T1 map image derived from T1W images acquired by use of an MP2RAGE sequence by the MRI apparatus 100; and parameter values set by the setting function 353. Further, for example, the generating function 354 may generate a calculated image by using: one MR image holding therein changes of TI, TE, and FA, the MR image having been obtained by the obtaining function 351; and parameter values set by the setting function 353.

The generating function 354 then displays the generated calculated image on the display 340.

FIGS. 5A to 5D and FIGS. 6A to 6D are diagrams illustrating specific examples of calculated images generated by the image processing apparatus 300 according to the first embodiment. FIGS. 5A to 5D and FIGS. 6A to 6D illustrate examples in a case where calculated images of FLAIR images are generated.

FIG. 5A illustrates an example of a known contrast ratio corresponding to a FLAIR image set in the contrast ratio table. Further, FIG. 5B illustrates an intended FLAIR image. Furthermore, FIG. 5C illustrates an example of a calculated image generated in a state before automatic setting of parameter values according to this embodiment is executed. Moreover, FIG. 5D illustrates an example of a calculated image generated after the automatic setting of parameter values according to this embodiment is executed.

For example, as illustrated in FIG. 5A, it is assumed that in the contrast ratio table, a known contrast ratio corresponding to a FLAIR image has been set as grey matter: white matter:cerebrospinal fluid=2.1:1:0. The intended FLAIR image illustrated in FIG. 5B is a FLAIR image having the contrast ratio illustrated in FIG. 5A obtained, among a region of grey matter (GM), a region of white matter (WM), and a region of cerebrospinal fluid (CSF). This FLAIR image is, for example, a FLAIR image suitable interpretation, or a FLAIR image of the same subject that has been acquired in the past.

As illustrated in FIG. 5C, for example, if a calculated image is generated in a state before automatic setting of parameter values according to this embodiment is executed, even if the same parameter values as the intended FLAIR image are used, due to errors in the T1 value, T2 value, and PD value generated at the time of data collection, the calculated image obtained does not necessarily have the same contrast as the intended FLAIR image.

In contrast, for example, as illustrated in FIG. 5D, if a calculated image is generated after automatic setting of parameter values according to this embodiment is executed, the same contrast as the intended FLAIR image is realized among the grey matter region (GM), the white matter region (WM), and the cerebrospinal fluid region (CSF).

As illustrated in FIG. 5D, for example, greater contrast is generated between a region of an abnormal part (a T2 lesion: a part having an abnormal T2 value as seen in multiple sclerosis) and its periphery reflecting the T1 value, T2 value, and PD value derived based on the set parameter values of TR, TE, and TI. Thereby, an abnormal part is able to be detected in a calculated image, similarly to ordinary interpretation of FLAIR images.

Further, FIG. 6A illustrates, similarly to FIG. 5A, an example of a known contrast ratio corresponding to a FLAIR image set in the contrast ratio table. FIG. 6B illustrates relations between TI and signal values in a grey matter region (GM), a white matter region), a cerebrospinal fluid region (CSF), and an abnormal part region (T2 lesion), when TR=8000. Further, FIG. 6C illustrates relations between TE and signal values in the respective regions, when TR=8000 and TI=2900. Furthermore, FIG. 6D illustrates relations between TE and signal values in the respective regions, when TR=8000 and TI=2580.

For example, as illustrated FIGS. 6B to 6D, since the signal values in each region change also according to the measured T1 values, T2 values, and PD values, variations are somewhat caused inevitably among measurements. That is, intended contrast is not obtained with fixed parameter values.

For example, as illustrated in FIG. 6A, it is assumed that in the contrast ratio table, a known contrast ratio corresponding to a FLAIR image has been set as grey matter: white matter:cerebrospinal fluid=2.1:1:0. In this case, for example, as illustrated in FIG. 6B, it is assumed that as a result of change of TI with TR=9000 in automatic setting of parameter values according to this embodiment, a state where TI=2900 before the automatic setting of parameter values is executed is brought into a state where TI=2580 after the automatic setting of parameter values is executed.

For example, as illustrated in FIG. 6C, when TE is changed with TR=8000 and TI=2900, signal values in the cerebrospinal fluid region (CSF) remain, and thus differences between signal values in the abnormal part region (T2 lesion) and signal values in the grey matter region (GM) and white matter region (WM) are decreased (see, for example, the signal values where TE=80).

In contrast, for example, as illustrated in FIG. 6D, if TE is changed with TR=8000 and TI=2580, signal values in the cerebrospinal fluid region (CSF) become 0, and thus differences between signal values in the abnormal part region (T2 lesion) and signal values in the grey matter region (GM) and white matter region (I) are increased (see, for example, the signal values where TE=80).

As described above, by automatic setting of parameter values used in generation of a calculated image, based on a known contrast ratio corresponding to a specified image type; a calculated image that is substantially an image that has been intended to be obtained (a FLAIR image in this example) is obtained. As illustrated in FIGS. 6C and 6D, for example, greater contrast is generated between the abnormal part region (T2 lesion) and its periphery reflecting the T1 value, T2 value, and PD value derived based on the set parameter values of TR, TE, and TI. Thereby, an abnormal part is able to be detected in a calculated image, similarly to ordinary interpretation of FLAIR images.

As described above, in this embodiment, by a contrast ratio among a grey matter region (GM), a white matter region (WM), and a cerebrospinal fluid region (CSF) in a calculated image being made the same as that of an intended FLAIR image, a contrast ratio between an abnormal part and its periphery in the calculated image is able to be improved. This is different from ordinary gain adjustment.

Hereinbefore, the functions that the processing circuitry 350 has have been described. For example, in this embodiment, the processing functions executed by the obtaining function 351, the dividing function 352, the setting function 353, and the generating function 354 are stored in the storage 320, in a program format executable by a computer. The processing circuitry 350 is a processor that realizes a function corresponding to each program by reading and executing the program from the storage 320. In other words, a processing circuitry that has read the programs has the respective functions illustrated in the processing circuitry 350 in FIG. 1.

Although FIG. 1 illustrates an example of the case where the processing functions executed by the obtaining function 351, the dividing function 352, the setting function 353, and the generating function 354 are implemented by the single processing circuitry 350, the embodiment is not limited to this example. For example, the processing circuitry 350 may be formed of a combination of plural independent processors, and the functions may be implemented by these processors respectively executing the programs. Further, any of the processing functions that the processing circuitry 350 has may be implemented by being distributed to or integrated into plural processing circuitries or a single processing circuitry, as appropriate. Further, according to the above description of the first embodiment, the single storage 320 stores therein the programs corresponding to the processing functions, but plural storages may be distributedly arranged, and the processing circuitry 350 may be configured to read the corresponding programs from the individual storages.

FIG. 7 is a flow chart illustrating a procedure of processing related to generation of a calculated image executed by the image processing apparatus 300 according to the first embodiment. For example, as illustrated in FIG. 7, in the image processing apparatus 300 according to this embodiment, firstly, the obtaining function 351 obtains an input image related to a brain of a subject from the MRI apparatus 100 or the image storing apparatus 200 (Step S101).

Thereafter, the dividing function 352 divides a region of the brain in the input image related to the brain, into plural regions (Step S102).

Further, the setting function 353 receives specification of an image type from an operator, via the input interface 330 (Step S103). Thereafter, the setting function 353 obtains a known contrast ratio corresponding to the specified image type, by referring to the contrast ratio table stored in the storage 320 (Step S104).

The setting function 353 then sets parameter values for generation of a calculated image, such that contrast among regions included in the plural regions divided by the dividing function 352 satisfies the obtained contrast ratio (Step S105).

Thereafter, the generating function 354 generates a calculated image by using the parameter values set by the setting function 353 (Step S106), and displays the generated calculated image on the display 340 (Step S107).

Step S101 is implemented by, for example, the processing circuitry 350 calling and executing a predetermined program corresponding to the obtaining function 351, from the storage 320. Further, Step S102 is implemented by, for example, the processing circuitry 350 calling and executing a predetermined program corresponding to the dividing function 352, from the storage 320. Furthermore, Steps S103 to S105 are implemented by, for example, the processing circuitry 350 calling and executing a predetermined program corresponding to the setting function 353, from the storage 320. Moreover, Steps S106 and S107 are implemented by, for example, the processing circuitry 350 calling and executing a predetermined program corresponding to the generating function 354, from the storage 320.

In FIG. 7, the processing of the dividing function 352 dividing a region of a brain into plural regions (Step S102), and the processing of the setting function 353 receiving specification of an image type from an operator and obtaining a known contrast ratio corresponding to the specified image type from the contrast ratio table (Steps S103 and S104) may be executed in the reverse order, or may be executed concurrently.

As described above, according to the first embodiment, based on quantitative images, a desired image type, and a contrast ratio among regions, parameter values allowing a calculated image to be obtained are able to be automatically set, the calculated image having the same contrast as an MR image that has conventionally been obtained by imaging. Thereby, adjustment of parameter is no longer needed, and the examination time is able to be shortened. Further, by automatic setting of parameters of a calculated image, the workflow is able to be improved.

Furthermore, according to the first embodiment, since a calculated image having a contrast ratio among regions optimized to be a specific contrast ratio is generated, luminance values in specific regions in a past calculated image and the present calculated image become the same. In addition, in the remaining regions, when there has been no change, luminance values become the same, but when there has been a change, their luminance values differ from each other, and thus follow-up observation is able to be performed easily.

Figure 8B:
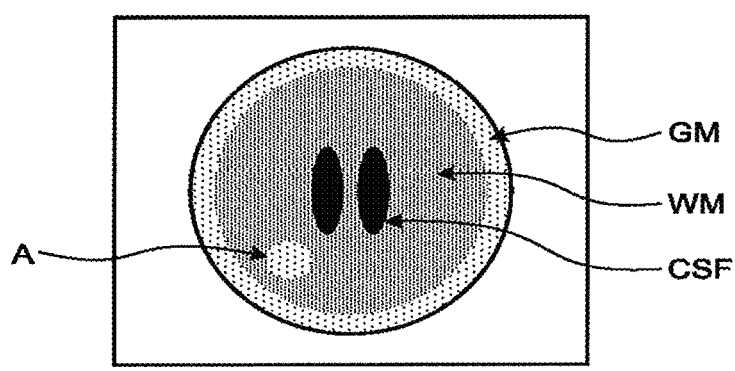

FIGS. 8A and 8F are diagrams illustrating an example of effects according to the first embodiment. FIG. 8A illustrates an example of a past calculated image generated by the image processing apparatus 300 according to this embodiment, and FIG. 8B illustrates an example of a present calculated image generated by the image processing apparatus 300 according to this embodiment.

As described above, according to the first embodiment, a calculated image is generated correspondingly to a contrast ratio set in the contrast ratio table. Therefore, for example, if there is no change in the characteristics, like in the grey matter regions (GM), the white matter regions (WM), and the cerebrospinal fluid regions (CSF) in the respective calculated images illustrated in FIG. 8A and FIG. 8B, luminance values in each region remain the same. In contrast, if there is an abnormal region A where there is a change in its characteristics between the past and the present, as illustrated in FIG. 8A and FIG. 8B, contrast with the abnormal region A differs between the past calculated image and the current calculated image.

Thus, according to the first embodiment, a calculated image suitable for diagnosis is able to be obtained.

With respect to the above described first embodiment, an example of the case where the setting function 353 obtains a known contrast ratio corresponding to a specified image type by referring to the contrast ratio table stored in the storage 320 has been described, but the embodiment is not limited to this example. For example, the setting function 353 may obtain a known contrast ratio corresponding to a specified image type by referring to an MR image acquired in the past or a calculated image generated in the past.

In that case, when parameter values are derived by use of a contrast ratio for a region of an abnormal part in an image acquired in the past, luminance values of most of the regions in the generated calculated image differ from those of the past image. Therefore, the setting function 353 does not use a contrast ratio for an abnormal part region in derivation of parameter values.

For example, for each of plural different combinations of regions included in an image acquired in the past, the setting function 353 derives parameter values based on a contrast ratio among the regions. From the plural parameter values derived, the setting function 353 regards largely different parameter values as outliers, and adopts parameter values that are the same as optimum parameter values.

For example, it is assumed that a contrast ratio between a grey matter region (GM) and a white matter region in a past image is 1:3, and parameter values derived therefrom are TE=a, TR=b, and TI=c. Further, it is assumed that a contrast ratio between a grey matter region (GM) and a cerebrospinal fluid region (CSE) in the past image is 1:0.1, and parameter values derived therefrom are TE=x, TR=y, and TI=z. Furthermore, it is assumed that a contrast ratio between a thalamus region and a cerebrospinal fluid region (CSF) in the past image is 1:0.1, and parameter values derived therefrom are TE=x, TR=y, and TI=z.

In this case, for example, the setting function 353 regards the parameter values derived from the contrast ratio between the grey matter region (GM) and the white matter region (WM) as outliers, and adopts, as optimum parameter values, the parameter values derived from the contrast ratio between the grey matter region (GM) and the cerebrospinal fluid region (CSF) and the contrast ratio between the thalamus region and the cerebrospinal fluid region (CSF).

Further, with respect to the above described first embodiment, an example of the case where an image type is specified by an operator has been described, but the embodiment is not limited to this example. For example, an image type to be processed may be specified beforehand and stored in the storage 320. In this case, for example, the setting function 353 sets parameter values used in generation of a calculated image, such that contrast among regions included in plural regions of a brain divided by the dividing function 352 becomes a known contrast ratio corresponding to the image type stored in the storage 320.

The number of image types stored in the storage 320 may be plural. In that case, the setting function 353 sets parameter values used in generation of calculated images, for all of the image types stored in the storage 320. For example, the generating function 354 generates a calculated image for each of all of the image types stored in the storage 320, and displays the generated calculated images in turn or concurrently, on the display 340.

With respect to the above described first embodiment, an example of the case where the setting function 353 refers to the contrast ratio table and the parameter range table stored in the storage 320 and sets parameter values used in generation of a calculated image has been described, but the embodiment is not limited to this example.

For example, the setting function 353 may set parameter values by using a learnt model obtained by machine learning using, as a data set for learning, quantitative images, image types, and correct answer values related to parameter values used in generation of calculated images.

For example, the setting function 353 uses deep learning as a method of machine learning.

In this case, for example, the setting function 353 generates a learnt model by deep learning having, as a learning data set: abundant quantitative images, such as T1 map images, T2 map images, and PD images; image types, such as T1W image, T2W image, and FLAIR image; and correct answer values related to parameter values of TR, TE, and TI used when calculated images of these image types are generated from these quantitative images.

Used as the correct answer values related to parameter values are, for example, values actually set as appropriate parameter values by a doctor or doctors when calculated images were used in past diagnosis. Or, as the correct answer values related to parameter values, for example, values actually set by use of the above described contrast ratio table and parameter range table are used.

As described above, by use of a learnt model obtained by deep learning, as compared to a case where parameter values are set by reference to the contrast ratio table and the parameter range table as described above, parameter values are able to be set in a shorter period of time.

The method of machine learning used by the setting function 353 is not limited to deep learning, and other methods may be used.

For example, the setting function 353 may use, as a method of machine learning, nonlinear discriminant analysis, support vector machine (SVM), random forest, or Naïve Bayes.

Support vector machine is a statistical method of forming a two-class pattern classifier by using a linear input element. Support vector machine is a statistical method of learning parameters of the linear input element, based on finding of a margin maximizing hyperplane from training data, the margin maximizing hyperplane being where distances from data points are maximized. Further, random forest is a statistical method of performing ensemble learning using multiple decision trees learnt from training data randomly sampled. Furthermore, Naïve Bayes is a statistical method of performing learning by using Bayes theorem.

In any of these methods, parameter values used in generation of a calculated image are able to be estimated by: generation of a learnt model through input of multiple data sets for learning corresponding to correct answer values; and use of the generated learnt model.

Further, with respect to the above described first embodiment, an example of the case where the setting function 353 sets parameter values such that contrast among regions included in plural regions divided by the dividing function 352 becomes a known contrast ratio has been described, but the regions targeted herein are not necessarily all of the regions divided by the dividing function 352.

For example, the setting function 353 receives an operation for specification of at least one region of plural regions divided by the dividing function 352 from an operator, and sets parameter values such that contrast among remaining regions excluding the specified region or regions from the plural regions satisfies a known relation.

In this case, for example, the setting function 353 displays an MR image of a brain used as an input image by the dividing function 352, on the display 340; and receives an operation for specification of an arbitrary position on the displayed MR image via the input interface 330, from the operator. The setting function 353 then identifies a region including the position specified by the operator, from plural regions of the brain obtained from the input image, and sets parameter values such that contrast among remaining regions excluding the identified region satisfies a known relation.

As described above, by exclusion of the region specified by the operator from the target, a region where an abnormal part, such as a tumor, has been generated, or a region where artifacts tend to be generated (for example, a region peripheral to a blood vessel) is able to be excluded from the regions used in setting of parameter values; and parameter values allowing a calculated image to be obtained are able to be set more accurately, the calculated image having the same contrast as an MR image that has been obtained by imaging.

Further, with respect to the above described first embodiment, an example of the case where the setting function 353 sets parameter values such that contrast among regions included in plural regions of a brain becomes a known contrast ratio corresponding to a specified image type has been described, but the embodiment is not limited to this example. For example, the setting function 353 may set parameter values used in generation of a calculated image, such that contrast between a region related to a specified disease and another region is emphasized. Thus, hereinafter, an example of such a case will be described as a second embodiment.

Second Embodiment

FIG. 9 is a diagram illustrating an example of a configuration of an image processing apparatus according to the second embodiment. In this second embodiment, points different from those of the first embodiment will be described mainly, and detailed description of component serving the same roles as the components illustrated in FIG. 1 will be omitted by assignment of the same reference signs thereto. For example, as illustrated in FIG. 9, in this embodiment, the MRI apparatus 100, the image storing apparatus 200, and an image processing apparatus 1300, are communicatably connected via the network 400.

The image processing apparatus 1300 processes image data collected by the MRI apparatus 100. Specifically, the image processing apparatus 1300 obtains image data from the PRI apparatus 100 or the image storing apparatus 200 via the network 400, and stores the obtained image data in a storage provided in or outside the image processing apparatus 1300. Further, the image processing apparatus 1300 executes various types of image processing on the obtained image data, and displays the yet to be image-processed image data or the image-processed image data, on a display or the like. For example, the image processing apparatus 1300 is realized by a computer device, such as a work station.

Specifically, the image processing apparatus 1300 includes the NW interface 310, a storage 1320, the input interface 330, the display 340, and a processing circuitry 1350.

The storage 1320 stores therein various data. Specifically, the storage 1320 is connected to the processing circuitry 1350, and stores therein image data input thereto, or outputs image data stored therein, to the processing circuitry 1350, according to a command transmitted from the processing circuitry 1350. For example, the storage 1320 is realized by: a semiconductor memory element, such as a FAM or a flash memory; a hard disk; or an optical disk.

According to input operations received from an operator via the input interface 330, the processing circuitry 1350 controls the components included in the image processing apparatus 1300. Specifically, the processing circuitry 1350 causes the storage 1320 to store therein image data output from the NW interface 310. Further, the processing circuitry 1350 displays image data read from the storage 320, on the display 340. For example, the processing circuitry 1350 is realized by a processor.

Based on such a configuration, the image processing apparatus 1300 according to this embodiment has a function of calculatively generating a calculated image of an arbitrary image type after imaging, by using MR images acquired by the MRI apparatus 100 and arbitrary parameter values. Image types include, for example, T1W image, T2W image, and FLAIR image.

For example, the image processing apparatus 1300 has, similarly to the image processing apparatus 300 described with respect to the first embodiment, a function of generating a calculated image by synthetic MRI.

The image processing apparatus 1300 according to this embodiment is configured to be able to obtain a calculated image suitable for diagnosis.

For example, the mere obtainment of calculated images with parameter values that are the same as those for imaging as generally done may lead to loss of diagnostic use value of calculated images having contrast that has never been acquired conventionally.

For that reason, the image processing apparatus 1300 according to this embodiment is configured to be able to obtain a calculated image highly useful for diagnosis by automatically setting parameter values allowing a calculated image to be obtained, the calculated image having contrast enabling a targeted region to be easily identified visually.

Specifically, in this embodiment, the storage 1320 stores therein information indicating, for each disease, a region or regions of plural regions of a brain, the region or regions being related to the disease. The storage 1320 according to this embodiment is an example of the storage.

FIG. 10 is a diagram illustrating an example of a disease-related region table stored in the storage 1320 according to the second embodiment. For example, as illustrated in FIG. 10, the storage 1320 stores therein, for each disease, a disease-related region table associating regions in a brain, the regions being related to the disease, with relevance between the regions and the disease.

For example, the example illustrated in FIG. 10 illustrates a disease-related region table related to Alzheimer disease, and "Region #2", "Region #3", and Region #8" illustrated in FIG. 10 each represent a region in the brain. For example, the example in FIG. 10 illustrates that relevance between Alzheimer disease and Region #2 is "2", relevance between Alzheimer disease and Region #3 is "5", and relevance between Alzheimer disease and Region #8 is "4". Relevance referred to herein may be set, for example, based on a p-value obtained from literature, or may be set based on the number of times the region was referred to when a doctor or doctors made diagnoses.

Further, in this embodiment, the processing circuitry 1350 has the obtaining function 351, the dividing function 352, a setting function 1353, the generating function 354, and an updating function 1355. The dividing function 352 according to this embodiment is an example of the dividing unit. Further, the setting function 1353 according to this embodiment is an example of the setting unit. Furthermore, the generating function 354 according to this embodiment is an example the generating unit. Moreover, the updating function 1355 according to this embodiment is an example of an updating unit. The dividing unit, the setting unit, the generating unit, and the updating unit in this specification may be realized by mixture of hardware, such as circuits, and software.

The setting function 1353 sets parameter values used in generation of a calculated image related to a brain, such that a relation of contrast among regions included in plural regions of the brain divided by the dividing function 352 becomes a predetermined relation.

Specifically, the setting function 1353 sets parameter values used in generation of a calculated image generated by synthetic MRI and related to a brain, such that a relation of contrast among regions included in plural regions in the calculated image becomes a predetermined relation.

In this embodiment, the setting function 1353 determines a region related to a disease specified by an operator, by referring to the disease-related region table stored in the storage 1320, and sets parameter values used in generation of a calculated image such that contrast between the determined region and another region is emphasized.

For example, the setting function 1353 may set parameter values used in generation of a calculated image, such that contrast between a region related to a specified disease and a region peripheral to that region is emphasized.

Specifically, the setting function 1353 receives specification of a disease from an operator, via the input interface 330. For example, the setting function 1353 receives specification of a disease by displaying, for plural predetermined diseases, a of these diseases on the display 340, and receiving an operation for selection of a disease from the displayed list, from an operator.

Thereafter, the setting function 1353 determines a region related to the specified disease by referring to the disease-related region table stored in the storage 1320. For example, the setting function 1353 determines, as a region to be processed, a region of the brain regions set in the disease-related region table, the region having the highest relevance to the specified disease.

The setting function 1353 then sets parameter values used in generation of a calculated image, within predetermined ranges that have been determined beforehand respectively for the parameter values, such that a contrast ratio between the determined region and a region peripheral to that region is maximized.

For example, when parameter values of TE, TR, and TI used in generation of a calculated image are respectively TE, TR, and TI, a combination of these parameter values is expressed as a set θ, as follows.

$$\theta = \{TR, TE, TI\}$$

Further, the predetermined ranges of parameter values of TE, TR, and TI are respectively expressed as follows. The ranges of these parameter values are desirably set sufficiently widely.

$$TR_{min} < TR < TR_{max}, TE_{min} < TE < TE_{max}, TI_{min} < TI < TI_{max}$$

For example, when the number of regions of a brain divided by the dividing function 352 is N, a contrast ratio among the determined region and the other regions in a calculated image derived from the parameter values of the set θ is represented by a vector $C_\theta$ composed of a contrast ratio among these regions, as follows.

$$C_\theta = (c1_\theta, c2_\theta, c3_\theta, \ldots cN_\theta)$$

Further, a contrast ratio between a region peripheral to the specified region and the other regions is represented by a vector $C_{PERI}$ composed of a contrast ratio among these regions, as follows.

$$C_{PERI} = (c1_{PERI}, c2_{PERI}, c3_{PERI}, \ldots cN_{PERI})$$

In this case, the setting function 1353 searches for a combination $\theta_{optimized}$ of TE, TR, and TI, at which a distance $D(C_\theta - C_{PERI})$ between the vector $C_\theta$ and the vector $C_{PERI}$ is maximized, by using a function $D(\cdot)$ representing distance between vectors, as expressed below.

$$\theta_{optimized} = \mathrm{argmax}_\theta D(C_\theta - C_{PERI})$$

Specifically, the setting function 1353 sequentially derives values of the vector $C_\theta$ and the vector $C_{PERI}$ while sequentially changing each of TE, TR, and TI individually within a predetermined range, and further derives values of the distance $D(C_\theta - C_{PERI})$ between the vector $C_\theta$ and the vector $C_{PERI}$. The setting function 1353 then determines $\theta_{optimized}$, which is a combination of TE, TR, and TI, at which the distance $D(C_\theta - C_{PERI})$ is maximized.

For example, when changing each parameter value, the setting function 1353 does not necessarily change the parameter value to all of values in a range of parameter values obtained from the parameter range table. For example, the setting function 1353 derives the values of the distance $D(C_\theta - C_{PERI})$ between the vector $C_\theta$ and the vector $C_{PERI}$ while sequentially changing the parameter values such that the parameter values gradually depart from their initial values that are parameter values normally used when the MR images are acquired. The setting function 1353 then ends processing at a time point when the distance $D(C_\theta - C_{PERI})$ has a value larger than a predetermined threshold, and determines $\theta_{optimized}$, which is a combination of TE, TR, and TI, at that time point.

Thereafter, the setting function 1353 respectively sets parameter values used in generation of a calculated image, the parameter values being parameter values of TE, TR, and TI in the determined $\theta_{optimized}$. Thereby, parameter values used in generation of a calculated image are automatically set, such that contrast between a region related to a specified disease and a region peripheral to that region is emphasized.

The updating function 1355 updates, according to an operation from an operator, information stored in the storage 1320, the information indicating regions related to a disease.

Specifically, the updating function 1355 updates, according to an operation from an operator, a disease-related region table stored in the storage 1320.

For example, the updating function 1355 displays an image representing plural regions divided by the dividing function 352, on the display 340, and receives an operation based on an interpretation result of interpretation of the displayed image, from an operator, such as a doctor.

The updating function 1355 then updates a disease-related region table according to the operation received from the operator. For example, the updating function 1355 changes or deletes a brain region that has been in a disease-related region table related to a specific disease, or adds a new brain region into the disease-related region table. Or, for example, the updating function 1355 registers a disease-related region table related to a new disease, in the storage 1320, or deletes a disease-related region table related to a specific disease, from the storage 1320.

As described above, by the updating function 1355 updating, according to an operation from an operator, a disease-related region table stored in the storage 1320, for example; based on results of interpretation performed by plural doctors, information indicating regions related to diseases is able to be accumulated.

Hereinbefore, functions that the processing circuitry 1350 has have been described. For example, in this embodiment, the processing functions executed by the obtaining function 351, the dividing function 352, the setting function 1353, the generating function 354, and the updating function 1355 are stored in the storage 320, in a program format executable by a computer. The processing circuitry 1350 is a processor that realizes a function corresponding to each program by reading and executing the program from the storage 1320. In other words, a processing circuitry that has read the programs has the respective functions illustrated in the processing circuitry 1350 in FIG. 9.

Although FIG. 9 illustrates an example of the case where the processing functions executed by the obtaining function 351, the dividing function 352, the setting function 1353, the generating function 354, and the updating function 1355 are implemented by the single processing circuitry 1350, the embodiment is not limited to this example. For example, the processing circuitry 1350 may be formed of a combination of plural independent processors, and the functions may be implemented by these processors respectively executing the programs. Further, the processing functions that the processing circuitry 1350 has may be implemented by being distributed to or integrated into plural processing circuitries or a single processing circuitry, as appropriate. Further, according to the above description of the second embodiment, the single storage 1320 stores therein the programs corresponding to the processing functions, but plural storages may be distributedly arranged, and the processing circuitry 1350 may be configured to read the corresponding programs from the individual storages.

FIG. 11 is a flow chart illustrating a procedure of processing related to updating of a disease-related region table executed by the image processing apparatus 1300 according to the second embodiment. For example, as illustrated in FIG. 11, in the image processing apparatus 1300 according to this embodiment, firstly, the obtaining function 351 obtains an input image related to a brain of subject, from the MRI apparatus 100 or the image storing apparatus 200 (Step S201). For example, the obtaining function 351 obtains a T1W image acquired by use of a Magnetization Prepared Rapid Gradient Echo (MPRAGE) sequence by the MRI apparatus 100.

Thereafter, the dividing function 52 divides a region of the brain in the input image related to the brain, into plural regions (Step S202).

The updating function 1355 then displays an image representing the plural regions divided by the dividing function 352, on the display 340 (Step S203), and receives an operation based on an interpretation result of interpretation of the displayed image, from an operator, such as a doctor (Step S204). Thereafter, according to the received operation, the updating function 1355 updates information indicating regions related to a disease (a disease-related region table) (Step S205).

Step S201 is implemented by, for example, the processing circuitry 1350 calling and executing a predetermined program corresponding to the obtaining function 351, from the storage 1320. Further, Step S202 is implemented by, for example, the processing circuitry 1350 calling and executing a predetermined program corresponding to the dividing function 352, from the storage 1320. Furthermore, Steps S203 to S205 are implemented by, for example, the processing circuitry 1350 calling and executing a predetermined program corresponding to the updating function 1355, from the storage 1320.

Herein, an example of the case where an image for interpretation is displayed by the updating function 1355 has been described, but the embodiment is not limited to this example. For example, the setting function 1353 in this embodiment may set parameter values similarly to the setting function 353 described with respect to the first embodiment, and the generating function 354 may generate a calculated image for interpretation by using the set parameter values.

Figure 12:
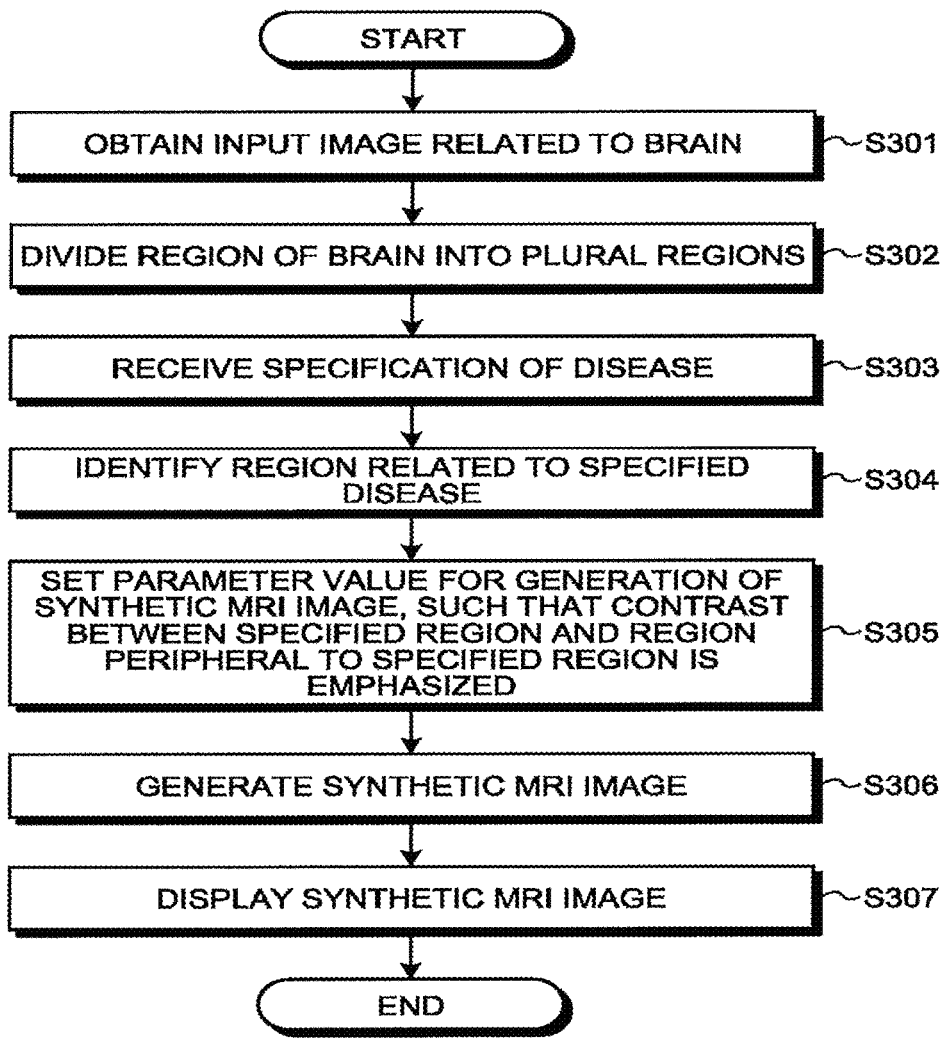
FIG. 12 is a flow illustrating a procedure of processing related to generation of a calculated image executed by the image processing apparatus according to the second embodiment.

FIG. 12 is a flow chart illustrating a procedure of processing related to generation of a calculated image executed by the image processing apparatus 1300 according to the second embodiment. For example, as illustrated in FIG. 12, in the image processing apparatus 1300 according to this embodiment, firstly, the obtaining function 351 obtains an input image related to a brain of a subject, from the MRI apparatus 100 or the image storing apparatus 200 (Step S301).

Thereafter, the dividing function 352 divides a region of the brain in the input image related to the brain, into plural regions (Step S302).

Further, the setting function 1353 receives specification of a disease from an operator, via the input interface 330 (Step S303). Thereafter, the setting function 1353 determines a region related to the specified disease, by referring to a disease-related region table stored in the storage 1320 (Step S304).

The setting function 1353 then sets parameter values for generation of a calculated image, such that a contrast ratio between the determined region and a region peripheral to the region is emphasized (Step S305).

Thereafter, the generating function 354 generates a calculated image by using the parameter values set by the setting function 1353 (Step S306), and displays the generated calculated image on the display 340 (Step S307). The calculated image displayed then may be an image not assigned with a specific name, such as T1W image, T2W image, or FLAIR image.

Step S301 is implemented, for example, by the processing circuitry 1350 calling and executing a predetermined program corresponding to the obtaining function 351, from the storage 1320. Further, Step S302 is implemented by, for example, the processing circuitry 1350 calling and executing a predetermined program corresponding to the dividing function 352, from the storage 1320. Furthermore, Steps S303 to S305 are implemented by, for example, the processing circuitry 1350 calling and executing a predetermined program corresponding to the setting function 1353, from the storage 1320. Moreover, Steps S306 and S307 are implemented by, for example, the processing circuitry 1350 calling and executing a predetermined program corresponding to the generating function 354, from the storage 1320.

In FIG. 12, the processing of the dividing function 352 dividing a region of a brain into plural regions (Step S302) and the processing of the setting function 1353 receiving specification of a disease from an operator and determining a region related to the specified disease (Steps S303 and S304) may be executed in the reverse order, or may be executed concurrently.

As described above, according to the second embodiment, based on information on a disease and a region related to the disease, parameter values allowing a calculated image to be obtained are able to be set automatically, the calculated image having contrast enabling a targeted region to be easily distinguished visually. Thereby, a calculated image highly useful for diagnosis is able to be obtained. In addition, it becomes easier for a doctor to interpret a region related to a disease on a calculated image.

Further, calculated images having contrast allowing abnormal regions to be clearly recognized are generated, the abnormal regions having been qualitatively interpreted by experienced doctors, and thus even inexperienced doctors are able to interpret the abnormal regions. Further, pixel values obtained from a generated calculated image may be determined as imaging biomarkers. Furthermore, by automatic setting of parameters of a calculated image, the workflow is able to be improved.

Thus, according to the second embodiment, a calculated image suitable for diagnosis is able to be obtained.

With respect to the above described second embodiment, an example of the case where the storage 1320 stores therein regions related to a disease one by one in a disease-related region table has been described, but the embodiment is not limited to this example. For example, the storage 1320 may store therein, for each disease, information indicating a combination of at least two regions related to the disease. In this case, for example, the setting function 1353 determines a combination of regions related to a specified disease by referring to information stored in the storage 1320, and sets parameters used in generation of a calculated image, such that contrast among the regions included in the determined combination is emphasized.

Further, with respect to the above described second embodiment, an example of the case where the setting function 1353 determines, as a region to be processed, a region having the highest relevance to a specified disease, the region being among brain regions set in a disease-related region table, has been described, but the embodiment is not limited to this example. For example, the setting function 1353 may process plural regions of a brain, the plural regions having been set in a disease-related region table. In this case, for example, the setting function 1353 derives a distance $D(C_\theta-C_{DB})$ between a vector $C_\theta$ and a vector $C_{DB}$ for all of those regions, and identifies $\theta_{optimized}$ from the derived distances, $\theta_{optimized}$ being a combination of TE, TR, and TI, at which the distance $D(C_\theta-C_{DB})$ is maximized. Further, if plural regions are to be processed like this, the setting function 1353 may execute weighting according to relevance set in a disease-related region table when parameters are set for each region.

Further, with respect to the above described second embodiment, an example of the case where the setting function 1353 determines a region related to a specified disease by referring to a disease-related region table stored in the storage 1320 has been described, but the embodiment is not limited to this example. For example, the setting function 1353 may receive, from an operator, an operation for specification of a region related to a disease from plural regions of a brain, and set parameter values such that contrast between the region specified by the operator and the other regions is emphasized. The number of regions received from the operator then may be one or plural.

Further, in the above described second embodiment, an example of the case where a disease is specified by an operator has been described, but the embodiment is not limited to this example. For example, a disease to be processed may be specified beforehand and stored in the storage 1320. In this case, for example, the setting function 1353 determines a region related to the disease stored in the storage 1320 by referring to a disease-related region table stored in the storage 1320, and sets parameter values used in generation of a calculated image such that contrast between the determined region and the other regions is emphasized.

The number of diseases stored in the storage 1320 then may be plural. If the number of diseases stored in the storage 1320 is plural, the setting function 1353 sets parameter values used in generation of a calculated image, for all of the diseases stored in the storage 1320. The generating function 354 then, for example, generates a calculated image for each of all of the diseases stored in the storage 1320, and displays the generated calculated images in turn or concurrently, on the display 340.

Further, with respect to the above described second embodiment, an example of the case where the setting function 1353 sets parameter values used in generation of a calculated image such that contrast between a region related to a specified disease and the other regions is emphasized has been described, but the degree of emphasis of the contrast may also be made changeable.

For example, the setting function 1353 may receive an operation for specification of an emphasis degree for contrast, from an operator, and set parameter values, such that contrast between a region related to a specified disease and the other regions is emphasized at the specified emphasis degree.

In this case, for example, the setting function 1353 receives, from the operator, an operation for input of a value indicating the emphasis degree, via the input interface 330. Or, for example, the setting function 1353 receives, from the operator, an operation for selection of one level from plural emphasis degree levels stepwisely determined beforehand, like a large level, a medium level, and a small level.

Thereby, the operator is able to adjust the degree of emphasis of a region related to a disease, and the interpretation is facilitated.

Hereinbefore, the image processing apparatuses according to the first and second embodiments have been described. In each of the above described first and second embodiments, for example, when the setting function derives optimum parameter values for generation of a calculated image, the setting function may store the derived parameter values as a preset, in the storage. In this case, for example, the generating function later generates the calculated image by reusing the parameter values stored as the preset.

Further, with respect to the above described first and second embodiments, examples of the case where synthetic MRI is used as a technique for generation of calculated images have been described, but the embodiments are not limited to these examples. For example, instead of synthetic MRI, MR fingerprinting may be used. In MR fingerprinting, tissue quantitative values, such as T1 values, T2 values, and proton density (PD) values, are derived by comparison with a database and simulation through estimation.

Further, with respect to the above described first and second embodiments, examples of the case where the techniques disclosed by the present application are applied to the image processing apparatus have been described, but the embodiments are not limited to these examples. For example, the techniques disclosed by this application are applicable to MRI apparatuses. Thus, hereinafter, embodiments of an MRI apparatus will be described as third and fourth embodiments.

Third Embodiment

Figure 13:
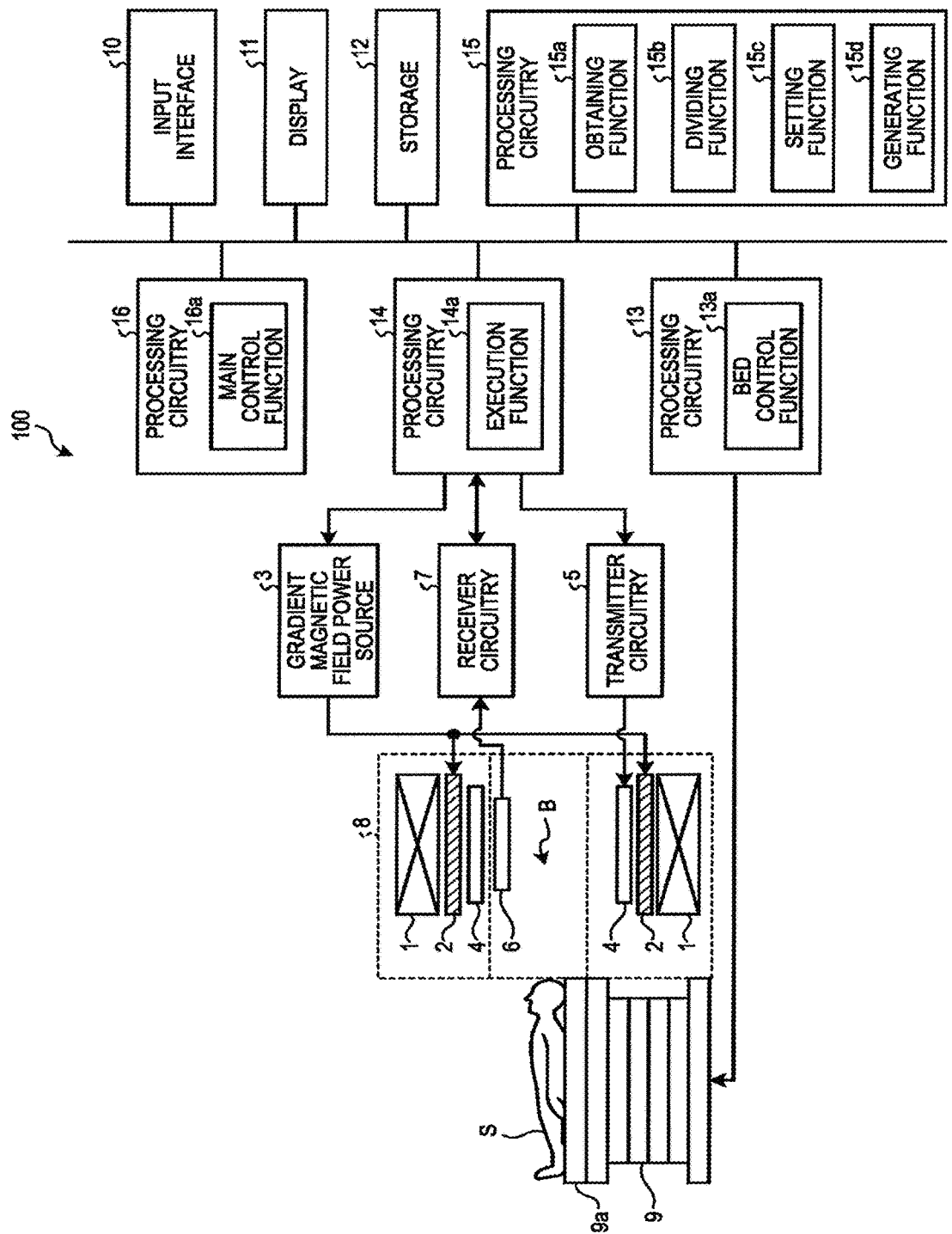
FIG. 13 is a diagram illustrating an example of a configuration of an MRI apparatus according to a third embodiment.

FIG. 13 is a diagram illustrating an example of a configuration of the MRI apparatus 100 according to the third embodiment. For example, as illustrated in FIG. 13, the MRI apparatus 100 according to this embodiment includes a static magnetic field magnet 1, a gradient coil 2, a gradient magnetic field power source 3, a transmitter coil 4, transmitter circuitry 5, a receiver coil 6, receiver circuitry 7, a gantry 8, a couch 9, an input interface 10, a display 11, a storage 12, and processing circuitries 13 to 16.

The static magnetic field magnet 1 is formed in an approximately cylindrical shape that is hollow (including a shape having an elliptical cross section orthogonal to a central axis of the cylinder), and generates a static magnetic field in a space inside the static magnetic field magnet 1. For example, the static magnetic field magnet 1 has: a cooling vessel formed in an approximately cylindrical shape; and a magnet, such as a superconducting magnet, immersed in a coolant (for example, liquid helium) filled in the cooling vessel. The static magnetic field magnet 1 may, for example, use a permanent magnet to generate the static magnetic field. Further, for example, the static magnetic field magnet 1 may be not formed in an approximately cylindrical shape, and may have a so-called open structure where a pair of magnets are arranged to oppose each other across an imaging space where a subject S is placed.

The gradient coil 2 is formed in an approximately cylindrical shape that is hollow (including a shape having an elliptical cross section orthogonal to a central axis of the cylinder), and is arranged inside the static magnetic field magnet 1. The gradient coil 2 includes three coils that generate gradient magnetic fields that are respectively along an x-axis, a y-axis, and a z-axis that are orthogonal to one another. The x-axis, y-axis, and z-axis form a device coordinate system specific to the MRI apparatus 100. For example, the direction of the x-axis is set in a horizontal direction, and the direction of the y-axis is set in a vertical direction. Further, the direction of the z-axis is set in the same direction as a magnetic flux of the static magnetic field generated by the static magnetic field magnet 1.

The gradient magnetic field power source 3 generates gradient magnetic fields that are respectively along the x-axis, y-axis, and axis in a space inside the gradient coil 2, by supplying electric current individually to each of the three coils included in the gradient coil By appropriate generation of the gradient magnetic fields that are respectively along the x-axis, y-axis, and z-axis, gradient magnetic fields that are respectively along a read-out direction, a phase encoding direction, and a slice direction are able to be generated.

Axes that are respectively along the read-out direction, the phase encoding direction, and the slice direction form a logical coordinate system for provision of a slice region or a volume region to be subjected to imaging. Hereinafter, the gradient magnetic field that is along the read-out direction will be referred to as a read-out gradient magnetic field, the gradient magnetic field that is along the phase encoding direction will be referred to as a phase encoding gradient magnetic field, and the gradient magnetic field that is along the slice direction will be referred to as a slice gradient magnetic field.

These gradient magnetic: fields are superimposed on the static magnetic field generated by the static magnetic field magnet 1, and is used for spatial positional information to be added to a magnetic resonance (MR) signal. Specifically, the read-out gradient magnetic field adds position information that is along the read-out direction, to an MR signal, by changing frequency of the MR signal according to a position in the read-out direction. Further, the phase encoding gradient magnetic field adds positional information in the phase encoding direction, to the MR signal, by changing phase of the MR signal along the phase encoding direction. Further, the slice gradient magnetic field is used for determination of the direction, the thickness, and the number of slice regions when the imaging region is the slice regions; and adds positional information along the slice direction, to the MR signal, by changing the phase of the MR signal according a position in the slice direction when the imaging region is a volume region.

The transmitter coil 4 is an RF coil that applies, based on a radio frequency (RF) pulse signal output from the transmitter circuitry 5, an RF magnetic field to the imaging space where the subject S is placed. Specifically, the transmitter coil 4 is formed in an approximately cylindrical shape that is hollow (including a shape having an elliptical cross section orthogonal to a central axis of the cylinder), and is arranged inside the gradient coil 2. Based on the RF pulse signal output from the transmitter circuitry 5, the transmitter coil 4 applies the RF magnetic field to the imaging space formed in a space inside the transmitter coil 4.

The transmitter circuitry 5 outputs an RF pulse signal corresponding to the Larmor frequency, to the transmitter coil 4.

The receiver coil 6 is an RF coil that receives an MR signal emitted from the subject S. For example, the receiver coil 6 is attached to the subject S placed inside the transmitter coil 4, and receives the MR signal emitted from the subject S due to influence of the RF magnetic field applied by the transmitter coil 4. The receiver coil 6 then outputs the received MR signal to the receiver circuitry 7. For example, as the receiver coil 6, a coil dedicated to each part to be imaged is used. Examples of the dedicated coil include a receiver coil for the head, a receiver coil for the neck, a receiver coil for the shoulder, a receiver coil for the chest, a receiver coil for the abdomen, a receiver coil for the lower limbs, and a receiver coil for the vertebral column.

Based on the MR signal output from the receiver coil, the receiver circuitry 7 generates MR signal data, and outputs the generated MR signal data to the processing circuitry 14.

Herein, an example of the case where the transmitter coil 4 applies the RF magnetic field and the receiver coil receives the MR signal is described, but modes of these RF coils are not limited to this example. For example, the transmitter coil 4 may further have a receiving function of receiving the MR signal, or the receiver coil 6 may further have a transmitting function of applying the RF magnetic field. If the transmitter coil 4 has the receiving function, the receiver circuitry 7 generates the R signal data also from the MR signal received by the transmitter coil 4. Further, if the receiver coil 6 has the transmitting function, the transmitter circuitry 5 outputs the RF pulse signal also to the receiver coil 6.

The gantry 8 accommodates therein the static magnetic field magnet 1, the gradient coil 2, and the transmitter coil 4. Specifically, the gantry 8 has a bore B that is formed cylindrically and is hollow, and accommodates therein each of the static magnetic field magnet 1, the gradient coil 2, and the transmitter coil 4, in a state where the static magnetic field magnet 1, the gradient coil 2, and the transmitter coil 4 surround the bore B. A space inside the bore B in the gantry 8 serves as the imaging space where the subject S is placed when imaging of the subject S is performed.

The couch 9 includes a couchtop 9a where the subject is placed, and the couchtop 9a is inserted inside the bore B in the gantry 8 when imaging of the subject S is performed. For example, the couch 9 is installed with its longitudinal direction being parallel to the central axis of the static magnetic field magnet 1.

The input interface 10 receives input operations for various instructions and various types of information, from an operator. Specifically, the input interface 10 is connected to the processing circuitry 16, converts an input operation received from the operator, into an electric signal, and outputs the converted electric signal to a control circuit. For example, the input interface 10 is realized by any of: a trackball for setting of a region of interest (ROI); switch buttons; a mouse; a keyboard; a touch pad, through which an input operation is performed by contact with an operating surface; a touch screen having a display screen and a touch pad that are integrated together; a non-contact input interface using an optical sensor; and a voice input interface. In this specification, the input interface 10 is not necessarily an input interface having physical operating parts, such as a mouse and a keyboard. For example, a processing circuitry that receives an electric signal corresponding to an input operation from an external input device provided separately from the MRI apparatus 100 and outputs this electric signal to a control circuit is also included in examples of the input interface 10.

The display 11 displays thereon various types of information and various images. Specifically, the display 11 is connected to the processing circuitry 16, converts data on various types of information and various images transmitted from the processing circuitry 16 into electric signals for display, and outputs the electric signals. For example, the display 11 is realized by a liquid crystal monitor, a cathode ray tube (CRT) monitor, or a touch panel.

The storage 12 stores therein various data. Specifically, the storage 12 stores therein MR signal data and image data. For example, the storage 12 is realized by: a semiconductor memory element, such as a random access memory (RAM) or a flash memory; a hard disk; or an optical disk.

The processing circuitry 13 has a bed control function 13a. For example, the processing circuitry 13 is realized by a processor. The bed control function 13a is connected to the couch 9, and controls operation of the couch 9 by outputting an electric signal for control, to the couch 9. For example, the bed control function 13a receives an instruction for movement of the couchtop 9a in the longitudinal direction, the vertical direction, or the horizontal direction, from an operator, via the input interface 10, and operates a drive mechanism for the couchtop 9a that the couch 9 has, so as to move the couchtop 9a according to the received instruction.

The processing circuitry 14 has an execution function 14a. The execution function 14a executes data collection for MR signal data by driving the gradient magnetic field pourer source 3, the transmitter circuitry 5, and the receiver circuitry 7, based on sequence execution data output from the processing circuitry 16. The sequence execution data are information defining a pulse sequence indicating a procedure for collecting MR signal data. Specifically, the sequence execution data are information defining: timing for supply of electric current to the gradient coil 2 by the gradient magnetic field power source 3, and strength of the electric current supplied; strength of the RF pulse signal supplied by the transmitter circuitry 5 to the transmitter coil 4, and timing for the supply; detection timing for detection of the MR signal by the receiver circuitry 7; and the like. For example, the processing circuitry 14 is realized by a processor.

Further, the execution function 14a receives, as results of execution of various pulse sequences, MR signal data from the receiver circuitry 7, and causes the storage 12 to store therein the received MR signal data. A collection of the MR signal data received by the execution function 14a is stored in the storage 12 as data forming a k-space, by being arranged two-dimensionally or three-dimensionally, according to positional information added by the read-out gradient magnetic field, the phase encoding gradient magnetic field, and the slice gradient magnetic field described already.

The processing circuitry 15 generates an image based on MR signal data stored in the storage 12. Specifically, the processing circuitry 15 generates an image by reading MR signal data stored in the storage 12 by the execution function 14a, and executing post-processing, that is, reconstruction processing, such as Fourier transform, on the read MR signal data. Further, the processing circuitry 15 causes the storage 12 to store therein image data of the generated image. For example, the processing circuitry 15 is realized by a processor.

The processing circuitry 16 has a main control function 16a. The main control function 16a executes overall control of the MRI apparatus 100 by controlling the components that the MRI apparatus 100 has. For example, the main control function 16a receives input of various parameters related to pulse sequences, from an operator, via the input interface 10, and generates sequence execution data based on the received parameters. The main control function 16a then executes various pulse sequences by transmitting the generated sequence execution data to the processing circuitry 14. Further, for example, the main control function 16a reads image data of an image requested by an operator, from the storage 12, and outputs the read image to the display 11. For example, the processing circuitry 16 is realized by a processor.

Based on such a configuration, the MRI apparatus according to this embodiment has a function of calculatively generating a calculated image of an arbitrary image type after imaging, by using MR images and arbitrary parameter values. Image types include, for example, T1 image, T2W image, and FLAIR image.

For example, the MRI apparatus 100 has, similarly to the image processing apparatus described with respect to the first embodiment, a function of generating a calculated image by synthetic MRI.

The MRI apparatus 100 according to this embodiment is configured to be able to obtain a calculated image suitable for diagnosis.

Specifically, in this embodiment, the storage 12 stores therein, similarly to the storage 320 described with respect to the first embodiment, for each image type, with respect to contrast among regions included in plural regions of a brain, information indicating a known contrast ratio corresponding to the image type. The storage 12 according to this embodiment is an example of the storage.

Further, in this embodiment, the storage 12 stores therein, similarly to the storage 320 described with respect to the first embodiment, for each image type, information defining ranges of parameter values, the ranges serving as conditions for setting of parameter values used in generation of a calculated image.

Furthermore, in this embodiment, the processing circuitry 15 has an obtaining function 15a, a dividing function 15b, a setting function 15c, and a generating function 15d. The dividing function 15b according to this embodiment is an example of the dividing unit. Further, the setting function 15c according to this embodiment is an example of the setting unit. Furthermore, the generating function 15d according to this embodiment is an example the generating unit. The dividing unit, the setting unit, and the generating unit in this specification may be realized by mixture of hardware, such as circuits, and software.

The obtaining function 15a has a function similar to that of the obtaining function 351 described with respect to the first embodiment. However, while the obtaining function 351 obtains input images from the MRI apparatus 100 or the image storing apparatus 200 in the first embodiment, the obtaining function 15a according to this embodiment obtains input images that are MR images related to a brain of a subject, from the storage 12.

The dividing function 15b has a function similar to that of the dividing function 352 described with respect to the first embodiment. Further, the setting function 15c has a function similar to that of the setting function 353 described with respect to the first embodiment. Furthermore, the generating function 15d has a function similar to that of the generating function 354 described with respect to the first embodiment.

In this embodiment, the input interface 10 and the display 11 respectively correspond to the input interface 330 and the display 340 described with respect to the first embodiment.

Hereinbefore, functions that the processing circuitry 15 has have been described. For example, in this embodiment, the processing functions executed by the obtaining function 15a, the dividing function 15b, the setting function 15c, and the generating function 15d are stored in the storage 12, in a program format executable by a computer. The processing circuitry 15 is a processor that implements a function corresponding to each program by reading and executing the program from the storage 12. In other words, a processing circuitry that has read the programs has the respective functions illustrated in the processing circuitry 15 in FIG. 13.

FIG. 13 illustrates an example of the case where the processing functions executed by the obtaining function 15a, the dividing function 15b, the setting function 15c, and the generating function 15d are implemented by the single processing circuitry 15, but the embodiment is not limited to this example. For example, the processing circuitry 15 may be formed of a combination of plural independent processors, and the functions may be implemented by these processors respectively executing the programs. Further, the processing functions that the processing circuitry 15 has may be implemented by being distributed to or integrated into plural processing circuitries or a single processing circuitry, as appropriate. Further, according to the shove description of the third embodiment, the single storage 12 stores therein the programs corresponding to the processing functions, but plural storages may be distributedly arranged, and the processing circuitry may be configured to read the corresponding programs from the individual storages.

Due to such a configuration, according to the third embodiment, effects similar to those of the first embodiment are achieved. That is, according to the third embodiment, examination time is able to be shortened by automatic setting of parameter values allowing a calculated image to be obtained, the calculated image having the same contrast as MR images that have been conventionally obtained by imaging.

Thus, according to the third embodiment, a calculated image suitable for diagnosis is able to be obtained.

Fourth Embodiment

Figure 14:
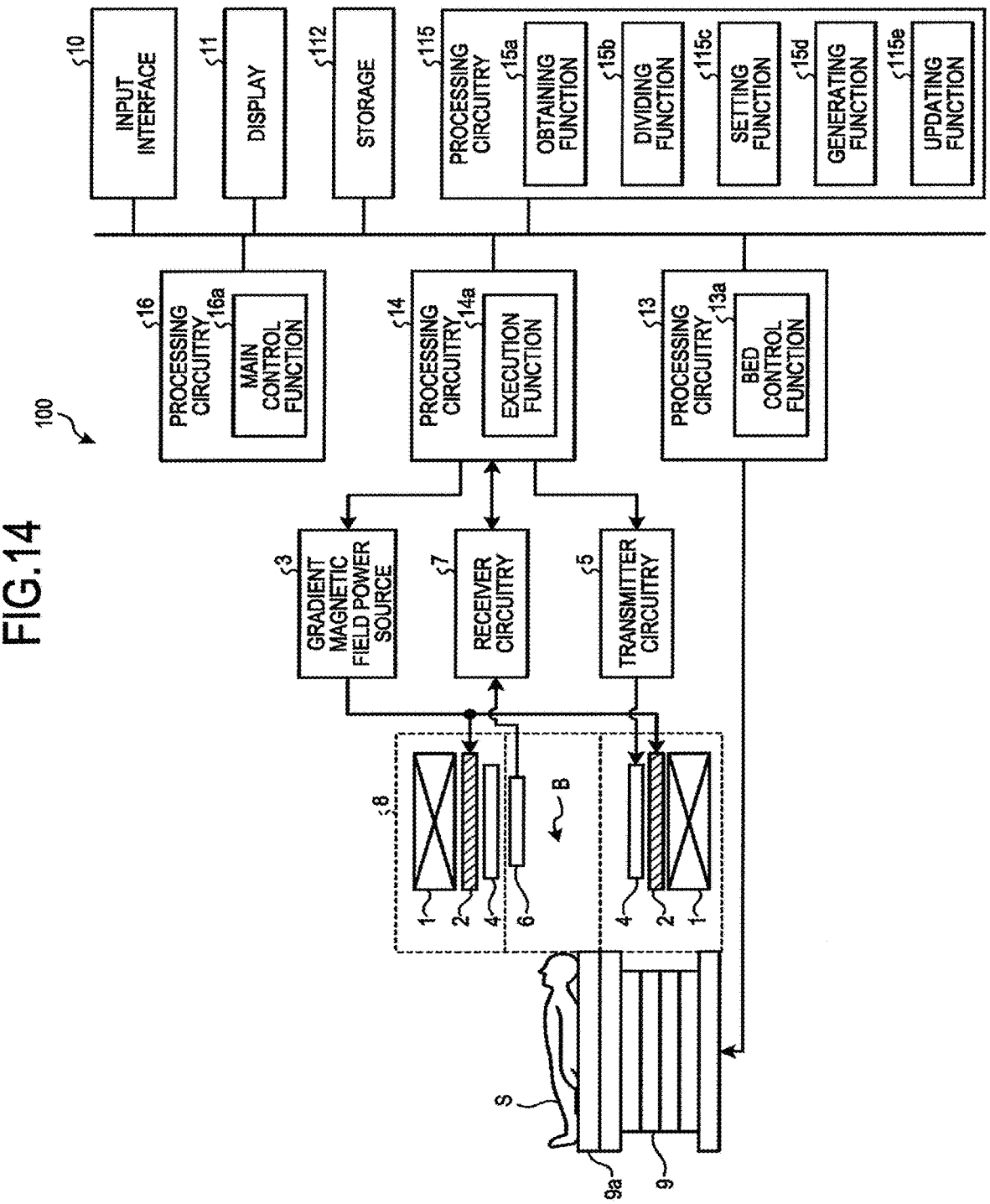
FIG. 14 is a diagram illustrating an example of a configuration of an MRI apparatus according to a fourth embodiment.

FIG. 14 is a diagram illustrating an example of a configuration of the MRI apparatus 100 according to the fourth embodiment. In this fourth embodiment, points different from those of the third embodiment will be described mainly, and detailed description of components serving the same roles as the components illustrated in FIG. 13 will be omitted by assignment of the same reference signs thereto. For example, as illustrated in FIG. 14, the MRI apparatus 100 according to this embodiment includes: the static magnetic field magnet 1; the gradient coil 2; the gradient magnetic field power source 3; the transmitter coil 4; the transmitter circuitry 5; the receiver coil 6; the receiver circuitry 7; the gantry 8; the couch 9; the input interface 10; the display 11; a storage 112; and the processing circuitries 13 and 14, a processing circuitry 115, and the processing circuitry 16.

The storage 112 stores therein various data. Specifically, the storage 112 stores therein MR signal data and image data. For example, the storage 112 is realized by: a semiconductor memory element, such as a random access memory or a flash memory; a hard disk; or an optical disk.

The processing circuitry 115 generates an image based on MR signal data stored in the storage 112. Specifically, the processing circuitry 115 generates an image by: reading MR signal data stored in the storage 112 by the execution function 14a; and executing post-processing, that is, reconstruction processing, such as Fourier transform, on the read MR signal data. Further, the processing circuitry 115 causes the storage 112 to store therein image data of the generated image. For example, the processing circuitry 115 is realized by a processor.

Based on such a configuration, the MRI apparatus 100 according to this embodiment has a function of calculatively generating a calculated image of an arbitrary image type after imaging, by using MR images and arbitrary parameter values. Image types include, for example, T1W image, T2W image, and FLAIR image.

For example, the MRI apparatus 100 has, similarly to the image processing apparatus described with respect to the second embodiment, a function of generating a calculated image by synthetic MRI.

The MRI apparatus 100 according to this embodiment is configured to be able to obtain a calculated image suitable for diagnosis.

Specifically, in this embodiment, the storage 112 stores therein, similarly to the storage 1320 described with respect to the second embodiment, for each disease, information indicating a region or regions of plural regions of a brain, the region or regions being related to the disease. The storage 1320 according to this embodiment is an example of the storage.

Further, in this embodiment, the processing circuitry 115 has the obtaining function 15a, the dividing function 15b, a setting function 115c, the generating function 15d, and an updating function 115e. The dividing function 15b according to this embodiment is an example of the dividing unit. Further, the setting function 115c according to this embodiment is an example of the setting unit. Furthermore, the generating function 15d according to this embodiment is an example the generating unit. Moreover, the updating function 115e according to this embodiment is an example of the updating unit. The dividing unit, the setting unit, the generating unit, and the updating unit in this specification may be realized by mixture of hardware, such as circuits, and software.

The setting function 115c has a function similar to that of the setting function 1353 described with respect to the second embodiment. Further, the updating function 115e has a function similar to that of the updating function 1355 described with respect to the second embodiment.

In this embodiment, the input interface 10 and the display 11 respectively correspond to the input interface 330 and the display 340 described with respect to the second embodiment.

Hereinbefore, functions that the processing circuitry 115 has have been described. For example, in this embodiment, the processing functions executed by the obtaining function 15a, the dividing function 15b, the setting function 115c, the generating function 15d, and the updating function 115e are stored in the storage 112, in a program format executable by a computer. The processing circuitry 115 is a processor that implements a function corresponding to each program by reading and executing the program from the storage 112. In other words, a processing circuitry that has read the programs has the respective functions illustrated in the processing circuitry 115 in FIG. 14.

FIG. 14 illustrates an example of the case where the processing functions executed by the obtaining function 15a, the dividing function 15b, the setting function 115c, the generating function 15d, and the updating function 115e are implemented by the single processing circuitry 115, but the embodiment is not limited to this example. For example, the processing circuitry 115 may be formed of a combination of plural independent processors, and the functions may be realized by these processors respectively executing the programs. Further, the processing functions that the processing circuitry 115 has may be implemented by being distributed to or integrated into plural processing circuitries or a single processing circuitry, as appropriate. Furthermore, according to the above description of the fourth embodiment, the single storage 112 stores therein the programs corresponding to the processing functions, but plural storages may be distributedly arranged, and the processing circuitry may be configured to read the corresponding programs from the individual storages.

Due to such a configuration, according to the fourth embodiment, effects similar to those of the second embodiment are achieved. That is, according to this fourth embodiment, a calculated image highly useful for diagnosis is able to be obtained by automatic setting of parameter values allowing a calculated image to be obtained, the calculated image having contrast enabling a targeted region to be easily identified visually.

Thus, according to the fourth embodiment, a calculated image suitable for diagnosis is able to be obtained.

In the above described embodiments, examples of the case where images of brains are targeted have been described, but the methods of generating calculated images described with respect to these embodiments are also applicable to a case where images of parts other than brains are targeted. In that case, for example, in each of these embodiments, the dividing function divides a region of a targeted part in an input image, into plural regions, by: using a template obtained by division of the region of the targeted part based on anatomical structures and functions; and fitting the template to the input image. Or, the dividing function divides a region of a targeted part in an input image into plural regions by using any of various segmentation(regional division) techniques.

Further, with respect to the above described embodiments, examples of the case where MR images are used have been described, but the embodiments are not limited to these examples. For example, even if medical images, which have been acquired by any other image diagnosis apparatus, such as an X-ray computed tomography (CT) apparatus, an ultrasound diagnostic device, or an X-ray diagnosis apparatus, are used, similar embodiments are able to be implemented in an image processing apparatus or that medical image diagnosis apparatus.

In addition, the term, "processor", used in the description of the embodiments above means, for example: central processing unit (CPU); a graphics processing unit (GPU); or a circuit, such as an application specific integrated circuit (ASIC) or a programmable logic device (for example, a simple programmable logic device (SPLD), a complex programmable logic device (CPLD), or a field programmable gate array (FPGA)). Instead of being stored in a storage, the programs may be directly incorporated in the circuit of a processor. In that case, by reading and executing the program incorporated in the circuit, the processor implements a function. Further, each of the processors according to the embodiments is not limited to being configured as a single circuit, and plural independent circuits may be combined together to be configured as one processor and implement their functions.

The programs executed by the processors are provided by being incorporated in the read only memories (ROM) or the storages beforehand. These programs may be provided by being recorded in a computer-readable storage medium, such as a compact disk ROM (CD-ROM), a flexible disk (ED), a recordable (CD-R), or a digital versatile disc (DVD), in a format that is installable or executable in those apparatuses. Further, the programs may be provided or distributed by being stored on a computer connected to a network, such as the Internet, and being downloaded via network. For example, these programs are configured as modules including the above described functional units. As to actual hardware, by a CPU reading and executing the programs from a storage medium, such as a ROM, the modules are loaded on the main storage, and generated on the main storage.

According to at least one of the embodiments described hereinbefore, a calculated image suitable for diagnosis is able to be obtained.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An image processing apparatus, comprising:
a processing circuitry configured to:
obtain a magnetic resonance (MR) image acquired by a magnetic resonance imaging apparatus, the MR image being related to a brain of a subject;
divide a region of the brain in the MR image, into plural regions;
set a parameter value used to generate a calculated image related to the brain by synthetic MRI, such that a relation of contrast among regions included in the plural regions in the calculated image becomes a relation of contrast among the regions, the relation being predetermined for an image type of the calculated image or for a disease of the subject; and
generate the calculated image by the synthetic MRI, by using a quantitative image derived from the MR image, and the set parameter value.

2. The image processing apparatus according to claim 1, wherein the processing circuitry sets the parameter value such that contrast among the regions satisfies a known contrast ratio corresponding to a specified image type.

3. The image processing apparatus according to claim 2, further comprising:
a storage configured to store therein, for each image type, with respect to the contrast among the regions, information indicating the known contrast ratio corresponding to the image type, wherein
the processing circuitry refers to the information stored in the storage, obtains the known contrast ratio corresponding the specified image type, and sets the parameter value such that the contrast among the regions satisfies the obtained contrast ratio.

4. The image processing apparatus according to claim 2, wherein the processing circuitry sets the parameter value by using a learnt model obtained by machine learning using, as a data set for learning, a quantitative image, an image type, and a correct answer value related to the parameter value used in the generation of the calculated image.

5. The image processing apparatus according to claim 2, wherein the processing circuitry receives, from an operator, an operation for specification of at least one region of the plural regions, and sets the parameter value such that contrast among remaining regions of the plural regions satisfies the known contrast ratio, the remaining regions excluding the at least one region.

6. The image processing apparatus according to claim 1, further comprising:
a storage configured to store therein information indicating, for each disease, a region of the plural regions, the region being related to the disease, wherein the processing circuitry refers to the information stored in the storage, determines a region related to a specified disease, and sets the parameter value such that contrast between the determined region and another region is emphasized.

7. The image processing apparatus according to claim 6, wherein the storage stores therein, for each disease, information indicating a combination of at least two regions related to the disease, and the processing circuitry refers to the information stored in the storage, determines a combination of regions related to the specified disease, and sets the parameter value such that contrast among the regions included in the determined combination is emphasized.

8. The image processing apparatus according to claim 6, wherein the processing circuitry further updates the information indicating the region related to the disease, according to an operation from an operator.

9. The image processing apparatus according to claim 6, wherein the processing circuitry sets the parameter value such that contrast between the region related to the specified disease and a region peripheral to the region is emphasized.

10. The image processing apparatus according to claim 6, wherein the processing circuitry receives, from an operator, an operation for specification of an emphasis degree for contrast, and sets the parameter value, such that contrast between the determined region and the another region is emphasized at the specified emphasis degree.

11. The image processing apparatus according to claim 1, wherein the processing circuitry receives, from an operator, an operation for specification of a region of the plural regions, the region being related to a disease, and sets the parameter value, such that contrast between the region specified by the operator and another region is emphasized.

12. The image processing apparatus according to claim 11, wherein the processing circuitry sets the parameter value such that contrast between the region related to the specified disease and a region peripheral to the region is emphasized.

13. The image processing apparatus according to claim 11, wherein the processing circuitry receives, from an operator, an operation for specification of an emphasis degree for contrast, and sets the parameter value, such that contrast between the specified region and the another region is emphasized at the specified emphasis degree.

14. The image processing apparatus according to claim 1, wherein the processing circuitry:

obtains a T1 weighted image acquired by the magnetic resonance imaging apparatus by use of a Magnetization Prepared 2 Rapid Gradient Echo (MP2RAGE) sequence, and a T1 map image derived from the T1 weighted image;

divides the region of the brain into the plural regions by using the T1 weighted image; and generates the calculated image by using the T1 map image and the parameter value.

15. An image processing apparatus, comprising:
a processing circuitry configured to:
obtain an input image related to a brain;
divide a region of the brain in the input image, into plural regions;
set a parameter value to generate a calculated image related to the brain, such that a relation of contrast among regions included in the plural regions in the calculated image becomes a relation of contrast among the regions, the relation being predetermined for an image type of the calculated image or for a disease of the subject; and
generate the calculated image by using the input image and the set parameter value.

16. A magnetic resonance imaging apparatus, comprising:
a processing circuitry configured to:
divide a region of a brain in a magnetic resonance (MR) image related to the brain, into plural regions;
set a parameter value to generate a calculated image related to the brain by synthetic MRI, such that a relation of contrast among regions included in the plural regions in the calculated image becomes a relation of contrast among the regions, the relation being predetermined for an image type of the calculated image or for a disease of the subject; and
generate the calculated image by the synthetic MRI, by using a quantitative image derived from the MR image, and the set parameter value.

17. A non-transitory computer-readable storage medium having plural computer-executable commands recorded therein, the plural computer-executable commands causing the computer to execute:

obtaining a magnetic resonance (MR) image acquired by a magnetic resonance imaging apparatus, the MR image being related to a brain;

dividing a region of the brain in the MR image, into plural regions;

setting a parameter value to generate a calculated image related to the brain by synthetic MM, such that a relation of contrast among regions included in the plural regions in the calculated image becomes a relation of contrast among the regions, the relation being predetermined for an image type of the calculated image or for a disease of the subject; and generating the calculated image by the synthetic MRI, by using a quantitative image derived from the MR image, and the set parameter value.

* * * * *